(12) United States Patent
Kohl

(10) Patent No.: US 9,340,841 B2
(45) Date of Patent: May 17, 2016

(54) MICRO-ORGANISMS CONTROLLING PLANT PATHOGENS

(71) Applicant: Jurgen Anton Kohl, Kleve (DE)

(72) Inventor: Jurgen Anton Kohl, Kleve (DE)

(73) Assignee: STICHTING DIENST LANDBOUWKUNDIG ONDERZOEK, Wageningen (NL)

(*) Notice: Subject to any disclaimer, the term of this patent is extended or adjusted under 35 U.S.C. 154(b) by 389 days.

(21) Appl. No.: 13/772,760

(22) Filed: Feb. 21, 2013

(65) Prior Publication Data

US 2013/0164320 A1 Jun. 27, 2013

Related U.S. Application Data

(62) Division of application No. 12/747,993, filed as application No. PCT/NL2008/050794 on Dec. 12, 2008, now Pat. No. 8,404,254.

(30) Foreign Application Priority Data

Dec. 14, 2007 (EP) .................................. 07123275

(51) Int. Cl.
*A01N 65/00* (2009.01)
*C12R 1/645* (2006.01)
*A01N 63/04* (2006.01)
*C12P 1/02* (2006.01)

(52) U.S. Cl.
CPC ............... *C12R 1/645* (2013.01); *A01N 63/04* (2013.01); *A01N 65/00* (2013.01); *C12P 1/02* (2013.01)

(58) Field of Classification Search
None
See application file for complete search history.

(56) References Cited

FOREIGN PATENT DOCUMENTS

| BR | PI0406274 | 9/2006 |
| WO | 2007/139382 | 12/2006 |

OTHER PUBLICATIONS

Luongo et al, "Potential of Fungal antagonists for biocontrol of *Fusarium* spp. in wheat and maize through competition in crop debris" Biocontrol Science and Technology, vol. 15, No. 3, May 2005, pp. 229-242.
Tatagiba et al, "Biological control of Botrytis cinerea in residues and flowers of rose (*Rosa hybrida*)", Phytoparasitica, vol. 26, No. 1, 1998, pp. 8-19.
Eden et al, "Biological control of Botrytis stem infection of greenhouse tomatoes" Plant Pathology (Oxford), vol. 45, No. 2, 1996, pp. 276-284.
Pereira et al, "The mycobiota of the weed *Mitracarpus hirtus* in Minas Gerais (Brazil), with particular reference to fungal pathogens for biological control" Australasian Plant Pathology, vol. 34, No. 1, 2005, pp. 41-50.
Scott et al, "Cladosporin, a new antifungal metabolite from Cladosporium cladosporioides" The Journal of Antibiotics Nov. 1971, vol. 24, No. 11, Nov. 1971, pp. 747-755.
Jacyno et al, "Isocladosporin, a biologically active isomer of cladosporin from Cladosporium cladosporioides" Journal of Natural Products (Lloydia), vol. 56, No. 8, 1993, pp. 1397-1401.
Fiss et al, "Isolation and characterization of epiphytic fungi from the phyllosphere of apple as potential biocontrol agents against apple scab (*Venturia inaequalis*)" Zeitschrift Fuer Pflanzenkrankheiten Und Pflanzenschutz, vol. 107, No. 1, Jan. 2000, pp. 1-11.
Kohl, "Replacement of Cooper Fungicides in Organic Production of Grapevine and Apple in Europe" [Online] Nov. 20, 2006; Retrieved from the internet: URL:http://www.rep-co.nl/documents/pub1%20executive%20summaries/REPCO-period%203%20Publishable%20executive%20summary.pdf>.
Kohl, "Replacement of Cooper Fungicides in Organic Production of Grapevine and Apple in Europe" [Online] Nov. 17, 2007 (Nov. 12, 2007); Retrieved from the internet: URL:http://www.rep-co.nl/documents/pub1%20executive%20summaries/REPCO%20Final_executive_summary.pdf>.

*Primary Examiner* — Robert A Zeman
(74) *Attorney, Agent, or Firm* — Mark T. Vogelbacker; Reed Smith LLP

(57) ABSTRACT

The invention relates to control of pathogen caused diseases on leaves, fruits and ears in plants, such as apple scab (*Venturia inaequalis* by treatment of plant with an isolate of *Cladosporium cladosporioides*. The treatment is effective in both prevention and treatment of the fungal infection.

13 Claims, 4 Drawing Sheets

B

MICRO-ORGANISMS CONTROLLING PLANT PATHOGENS

RELATED APPLICATIONS

Figure 1:
Figure 1:
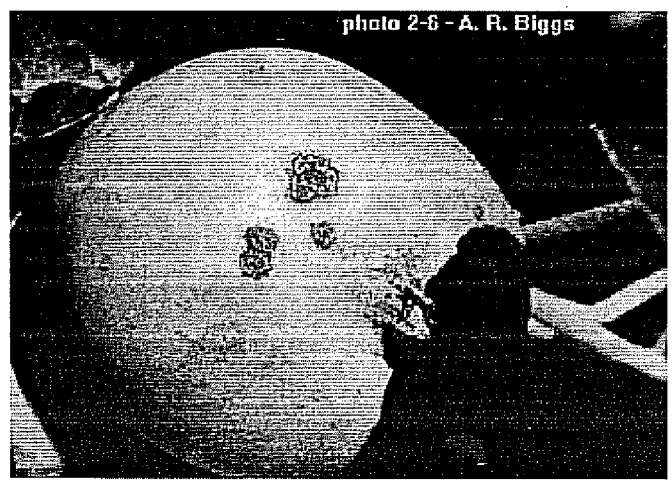

This application is a Divisional Patent Application of U.S. Ser. No. 12/747,993 filed on Jul. 22, 2010, which is now issued as U.S. Pat. No. 8,404,254. U.S. Ser. No. 12/747,993 is the United States National Stage of International Application No. PCT/NL2008/050794, filed Dec. 12, 2008, which was published as International Publication No. WO 2009/078710, and which claims benefit of European Patent Application No. 07123275.5 filed Dec. 14, 2007. All applications are incorporated by reference in their entirety herewith.

FIELD OF THE INVENTION

The invention relates to the field of plant pathogen control, particularly on leaves, fruits or ears, more particularly in fruit crops, such as apple, and particularly to the control of the fungal foliar disease apple scab (*Venturia inaequalis*).

BACKGROUND OF THE INVENTION

Apple scab is of major economic importance in the areas where apples are grown. If not controlled, the disease can cause extensive losses (70 percent or greater) where humid, cool weather occurs during the spring months. Losses result directly from fruit or pedicel infections, or indirectly from repeated defoliation which can reduce tree growth and yield.

Apple scab (see FIG. 1) can be observed on leaves, petioles, blossoms, sepals, fruit, pedicels, and less frequently, on young shoots and bud scales. The first lesions are often found on the lower surfaces of leaves as they emerge and are exposed to infection in the spring. Later, as the leaves unfold, both surfaces are exposed and can become infected. Young lesions are velvety brown to olive green and have feathery, indistinct margins. With time, the margins become distinct, but they may be obscured if several lesions coalesce. As an infected leaf ages, the tissues adjacent to the lesion thicken, and the leaf surface becomes deformed. Young leaves may become curled, dwarfed, and distorted when infections are numerous. The lesions may remain on the upper and lower leaf surface for the entire growing season; occasionally, the underlying cells turn brown and die, so that brown lesions are visible on both surfaces. The number of lesions per leaf may range from one or two to more than a hundred. The term "sheet scab" is often used to refer to leaves with their entire surfaces covered with scab. Young leaves with sheet scab often shrivel and fall from the tree. Infections of petioles and pedicels result in premature abscission of leaves and fruit, respectively. In late summer or early fall, lesions may appear whitish due to the growth of a secondary fungus on the lesion surface.

Lesions on young fruit appear similar to those on leaves, but as the infected fruit enlarge, the lesions become brown and corky. Infections early in the season can cause fruit to develop unevenly as uninfected portions continue to grow. Cracks then appear in the skin and flesh, or the fruit may become deformed. The entire fruit surface is susceptible to infection, but infections early in the season are generally clustered around the calyx end. Fruit infections that occur in late summer or early fall may not be visible until the fruit are in storage. This symptom is called "pin-point" scab, with rough circular black lesions ranging from 0.004 to 0.16 inch (0.1-4 mm) in diameter.

Although research in New York has shown that the scab fungus can overwinter in trees as conidia on bud scales, the pathogen generally overwinters in leaves and fruit on the orchard floor. Ascospores are the major source of primary inoculum and are produced within pseudothecia that develop in leaves during the winter months. In a typical year in most locations, the first mature ascospores are capable of causing infections at about the time of bud break or soon thereafter. Ascospores continue to mature and are discharged over a period of five to nine weeks, with peak discharge during the pink to petal fall phenological stages. The length of time required for infection to occur depends on the number of hours of continuous wetness on the leaves and the temperature during the wet period. Young leaves remain susceptible for five to eight days, but their lower surfaces may become infected in late summer. For fruit, the duration of the wet period required for infection increases with the age of the fruit, which remains susceptible until harvest. Once the fungus is established in the leaf or fruit, conidia form on the surface of the lesion and become the source of secondary inoculum for the remainder of the season. Conidia are disseminated to developing leaves and fruit by splashing rain and wind. Several secondary cycles of conidial infection may occur during the growing season depending upon the frequency of infection periods and the susceptibility of host tissue.

Management of apple scab is multifaceted, with resistant cultivars, sanitation, and chemicals all being used to some degree depending on the orchard system being used and the goals of the grower.

Most of the major apple cultivars are susceptible to the fungus, although this varies somewhat. More than 25 scab-resistant cultivars have been released, included Prima, Priscilla, Jonafree, Redfree, Liberty, Freedom, Goldrush, and Pristine. Most are adapted to the more northern apple-growing areas of the U.S. All scab-resistant cultivars vary in their susceptibility to other early-season diseases; and all are susceptible to the summer diseases. Some recently released apple cultivars that have not been bred specifically for resistance to scab show varying levels of scab susceptibility, also.

Prevention of pseudothecial formation in overwintering apple leaves would probably eliminate scab as a serious threat to apple production. Unfortunately, complete elimination of pseudothecia is not possible under orchard conditions with current methods.

Apple scab is controlled primarily with fungicide sprays. A variety of fungicide sprays with differing modes of action are available. When and how they are used depends upon their mode of action. Protectant fungicides prevent the spores from germinating or penetrating leaf tissue. To be effective, they must be applied to the surface of susceptible tissue before infection occurs. Occurrence of infection can, amongst others, be predicted with an accurate weather forecast. Protectant fungicides are applied routinely at 7 to 10 day intervals or according to anticipated infection periods.

Post infection fungicides control the scab fungus inside leaves and fruit. These chemicals can penetrate plant tissues to eliminate or inhibit lesion development. The ability of these fungicides to stop infections is limited to a few hours, or up to few days (depending upon the specific fungicide), and their effect often varies according to temperatures during the first 24 to 48 hours after infection. Some fungicides can inhibit the fungus even later into the incubation period (the time between infection and the appearance of symptoms). Eradication of scab lesions after they appear does not usually occur, but can be achieved with the proper rate and timing of certain fungicides. The selection of fungicides for management of scab is based on several factors, including the entire spectrum of other diseases that must be managed at that time, the potential for resistance in the scab fungus to the selected chemical, the history of the disease in a particular orchard, the final market for the fruit, and other social and economic factors. Good horticultural practices, such as proper site selection, tree spacing and annual pruning, facilitates better chemical control by improving spray coverage and reducing the length of wet periods. Chemical fungicides used in the treatment or prevention of apple scab include maneb, mancozeb, captan, pyrimethanil and tolylfluanide.

There is thus still need for a natural fungicide, which is effective for the control of apple scab, and which is environment-friendly and non-toxic for humans and/or animals.

SUMMARY OF THE INVENTION

The inventors have found two new isolates of *Cladosporium cladosporioides*, i.e. *C. cladosporioides* H39, as deposited on 13 Dec. 2007 under number CBS 122244 with the Centraal Bureau Schimmelcultures, Uppsalalaan 8, P.O. Box 85167, 3508AD UTRECHT, Baarn, The Netherlands and *C. cladosporioides* R406, as deposited on 13 Dec. 2007 under number CBS 122243 with the Centraal Bureau Schimmelcultures, Baarn, The Netherlands. Said isolates are useful in a composition to control a plant pathogen of leaves, fruits and ears. Such a composition is preferably useful for diseases wherein said plant pathogen is selected from the group consisting of apple scab (*Venturia inaequalis*), pear scab (*Venturia pirina*), leaf spot (*Blumeriella jaapi*), rose black spot (*Diplocarpon rosae/Marssonina rosae*), brown spot (*Stemphylium vesicarium*), powdery mildew (*Podosphaera leucotricha/Sphaerotheca pannosa*), begonia mildew (*Microsphaera begoniae*), strawberry powdery mildew (*Sphaerotheca macularis*), sooty blotch (*Gloeodes pomigena*), fly speck (*Zygophalia jamaicensis*), peach leaf curl (*Taphrina deformans*), brown rot/spur canker (*Monilia fructigena, M. laxa*), pear rust (*Gymnosporangium sabinae/G. fuscum*), canker (*Nectria galligena*), rose black spot (*Diplocarpon rosae*), rust on roses (*Phragmidium tuberculatum/Phragmidium* spp.), *Botrytis* spp. in various plants, *Mycosphaerella brassicicola* in cabbage, *Mycosphaerella fijiensis* in banana, *Alternaria* spp. in *Brassica*, potato and various other plants, *Fusarium* spp. especially in cereals including maize, *Phytophthora infestans* of potato and *Plasmopara viticola* in grapevine, more preferably wherein said fungal foliar pathogen is apple scab.

Further, in such a composition the *Cladosporium* is present as spores and further comprises a carrier for the *Cladosporium* spores, preferably wherein said carrier is glucose. Alternatively, the composition can comprise an extract of the *Cladosporium* of the invention.

In another embodiment, the invention comprises a method to control a pathogen in plants, comprising treating said plants with a composition according to the invention. Preferably, said composition is sprayed on the leaves, fruits or ears of the plant. Such a method for control of the pathogen comprises prevention of infection and/or a decrease of plant damage caused by said pathogen. Said method will be usable against any pathogen mentioned above, preferably against apple scab. A further embodiment in the present invention is the use of a *Cladosporium* isolate according to the invention, or a composition according to the invention for the prevention or treatment of infection of leaves, fruits or ears of a plant by a pathogen. Further comprised in the invention is a *Cladosporium* strain or a composition according to the invention for use in the control of a plant pathogen infection.

LEGENDS TO THE FIGURES

FIG. 1 Scab symptoms caused by *Venturia inaequalis* (Vi) on leaves (a) and fruit (b).

Figure 2:
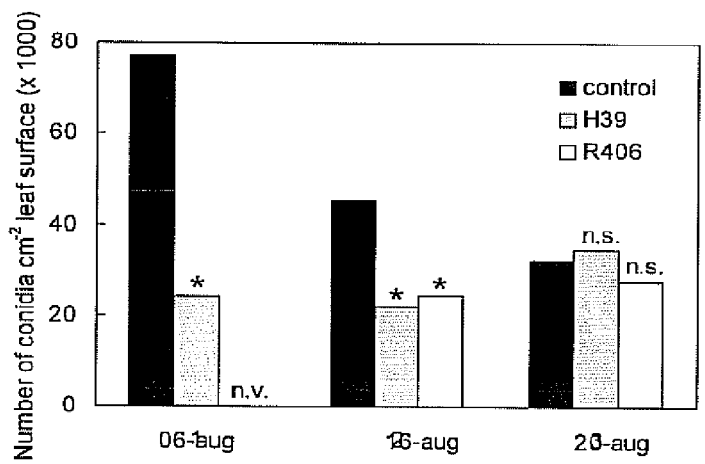

FIG. 2. Conidia production of Vi on apple leaves treated twice per week with *Cladosporium cladosporioides* H39 or R406 (approximately $2 \times 10^6$ viable spores $ml^{-1}$) in an organically managed orchard. Randwijk 2007. Statistically significant effects of individual treatments in comparison with the control treatment are indicated by '*'separately per sampling date; one-sided unprotected LSD-test; (=0.05). N.s.: no significant difference; n.v.: no value FIG. 3. Predicted infection periods, dates of spray applications of *Cladosporium cladosporioides* H39 and sulphur, and sampling dates (L: Labelling of new leaves; S: Sampling).

FIG. 4. Effect of treatments with conidia of *Cladosporium cladosporioides* H39 or sulphur on conidia production of *Venturia inaequalis*. Bars of the same sampling date with a common letter do differ significantly (LSD-test; =0.05).

FIG. 5. Effect of treatments with conidia of *Cladosporium cladosporioides* H39 or sulphur on scab severity. Bars with a common letter do differ significantly (LSD-test; =0.05).

DETAILED DESCRIPTION

As detailed above, apple scab is a disease with tremendous economical impacts for the apple growers. This is especially the case for apple scab control by organic farmers, who have few or no alternative chemical pesticides, especially now that some of the agents, which are commonly used are tending to be phased out because of environmental and general toxicity risks.

An alternative is being sought in the form of extracts from plants, since plant extracts have been described to be possible candidates for treating fungal diseases and since these would comply with the requirements for organic growing. Recently, the use of extracts from Yucca has been documented (WO 2007/139382).

However, next to plant extracts also natural occurring micro-organisms are useful in the control of plant pathogens. Especially many fungi are known because of their biocidal effects, such as *Penicillium* and *Trichoderma*. More specifically, there also exist fungi which are especially useful against plant pathogens. Also in the case of apple scab such fungi have been discovered, such as *Chaetomium globosum* (Boudrau, M. A. et al., 1987, Phytopathol. 77:1470-1475), *Microsphaeropsis ochracea* (Carisse, O. et al., 2000, Phytopathol. 90:31-37), *Ophiostoma* sp. and *Phoma* sp. (Ouimet, A., et al., 1997, Can. J. Bot. 75:632-639). General overviews may be found in Burr, T. J. et al., 1996, Biol. Control 6:151-157 and Fiss, M. et al., 2003, Z. Pflanzenkrankh. Pflanzenschutz, 110(6):513-523. Recently, it has been disclosed (Ziedan, E. H. E., 2006, Res. J. Agric. & Biol. Sci. 2(6):262-267) that an isolate of *Cladosporium cladosporioides*, derived from the phyllosphere of grapevine, administered together with benzoic acid was effective against the grapevine downey mildew causing fungus *Plasmopara viticola*. Also was found that particular isolates of *Cladosporium cladosporioides* can be used against *Botrytis* and *Fusarium* infections (Newhook, F. J., 1957, New Zealand Journal of Science and Technology 23:23-54. Eden et al., 1996, Plant Pathol. 45:276-284).

In the present invention it has now been discovered that two isolates of *Cladosporium cladosporioides* are effective against fungal foliar pathogenic diseases, such as apple scab. These two isolates are *Cladosporium cladosporioides* H39 and *Cladosporium cladosporioides* R406, deposited on 13 Dec. 2007 with the Centraal Bureau voor Schimmelcultures, Baarn, the Netherlands under nrs. CBS 122244 and CBS 122243, respectively. As is shown in the experimental section of the specification, these two new isolates had a clear effect on apple scab development, while other isolates of *Cladosporium cladosporioides* did not have any effect.

*Cladosporium cladosporioides* (Fresen.) de Vries belongs to the group of the *Fungi imperfecti* and its growth is characterized by colonies of about 3 cm in diameter when grown for seven days on potato-dextrose agar at 20° C. Colonies of *Cladosporium cladosporioides* are effuse, olive green or oliviceous brow, velvety; reverse on malt agar greenish black. Conidiophores are macronematous and micronematous, sometimes up to 350µ long but generally much shorter, 2-6µ thick, pale to mid olivaceous brown, smooth or verrucose. Ramo-conidia are 0-1 septated, up to 30µ long, 2-5µ thick, smooth or occasionally minutely verrucose. Conidia are formed in long branched chains, mostly 0-septated, ellipsoidal or limoniform, 3-11×2-5 (mostly 3-7×2-4)µ, pale olivaceous brown, most commonly smooth but verruculose in some strains (Ellis, M. B., 2001, Dematiaceous Hyphomycetes).

It has been reported that one of the metabolites, cladosporin, acts as antifungal. This cladosporin has been shown to have antibiotic properties (Scott, P. M. et al., 1971, J. Antibiotics 24:747-755). Yet, as already discussed above, it was found in our experiments that not all isolates of *Cladosporium cladosporioides* had an inhibitory effect on apple scab infection. Apparently, either cladosporin is not functional against *Venturia inaequalis*, or, more likely, the isolates of the fungus differ in their phenotype of cladosporin expression and secretion. Possibly, also other mechanisms of mode-of-action are involved in antagonism of H39 and R406 towards *Venturia inaequalis* and other plant pathogens.

*Cladosporium* spp. are common epiphytic colonizers of leaf surfaces, often found in high densities (Dickinson, 1981). Epiphytic colonization by *Cladosporium* spp. is also reported for apple leaves (Fiss et al, 2000) and fruits (Teixido et al., 1999). Such epiphytic populations of *Cladosporium* spp. may contribute to naturally occurring intrinsic biological control. In this case, conservation biological control (Eilenberg et al., 2001) protecting such beneficial populations by avoiding fungicides with side effects on non-target populations (Teixido et al., 1999; (Walter et al., 2007) or even selectively stimulating such naturally occurring beneficial populations, e.g. by application specific nutrients, may contribute to scab prevention.

As is shown in the Examples, the two isolates of the present invention showed a clear effect in the control of apple scab. It is further submitted that not only apple scab but any fungal plant pathogen of leaves, fruits or ears can be controlled by said isolates. Said fungal foliar pathogen is selected from the group consisting of apple scab (*Venturia inaequalis*), pear scab (*Venturia pirina*), leaf spot (*Blumeriella jaapi*), rose black spot (*Diplocarpon rosae/Marssonina rosae*), brown spot (*Stemphylium vesicarium*), powdery mildews of various plants such as strawberry, roses and apple, sooty blotch (*Gloeodes pomigena*), fly speck (*Zygophalia jamaicensis*), peach leaf curl (*Taphrina deformans*), brown rot/spur canker (*Monilia fructigena, M. laxa*), pear rust (*Gymnosporangium sabinae/G. fuscum*), canker (*Nectria galligena*), rose black spot (*Diplocarpon rosae*), rust on roses (*Phragmidium tuberculatum/Phragmidium* spp.), *Botrytis* spp. in various plants, *Mycosphaerella brassicicola* in cabbage, *Mycosphaerella fijiensis* in banana, *Alternaria* spp. in *Brassica*, potato and various other plants, *Fusarium* spp. especially in cereals including maize, *Phytophthora* infestans of potato and *Plasmopara viticola* in grapevine, preferably wherein said fungal foliar pathogen is apple scab.

It appeared in the case of H39 that the way of culturing and the formulation of the fungus had a marked influence on the inhibitory effect. Conidia of *C. cladosporioides* H39 produced on oat meal agar were not effective under orchards conditions but those produced on oats in an fermenter consistently showed moderate effectivity. Microscopical observations showed that conidia produced on oats in an fermenter were larger than those produced on oat meal agar. The effect of growth medium on the spore quality of antagonists resulting in a better performance under environmental stress conditions has been demonstrated for several other antipathogenic fungi, e.g. cells of *Candida* sake produced on low-$a_w$-modified media (Teixido et al., 1999). Colonization of apple leaves by introduced fungi depends on the biology of the introduced species (Kinkel et al., 1989). In their case study, introduced populations of *C. globosum* significantly decreased within a few days in contrast to populations of *A. pullulans*. In the below experiments, the inhibitory compositions were applied at 3 to 4 days interval to guarantee high populations level on the leaves. However, first results on population dynamics of *Cladosporium cladosporioides* indicate that after application of H39 such populations increased and that such treatment effects were found even after several weeks (see example 2).

Formulation of the fungus is important for the viability of the fungal spores contained in the composition that is applied to the plant. It has appeared that a formulation wherein glucose is used as carrier for the *Cladosporium* spores performs better than unformulated fungus.

Alternatively, an antifungal composition of the present invention may contain an extract of one or both of the *Cladosporium* isolates of the invention. Extracts of the two isolates can be obtained as described in the literature for other *Cladosporium* extracts, and can be readily obtained by a person of skill in the art (see e.g. Ding, L. et al., 2008, Current Microbiol., 56:229-235).

Further, the composition may contain additional compounds that are commonly used in spraying solutions, such as preservatives, surface active compounds, wetting agents, and the like. It is also possible to include further antifungal compounds or organisms in the composition to enhance the inhibitory effect. In such a case, lower levels of traditional chemical fungicides can be used, thereby enabling a desired reduction in the amount of fungicides. As discussed above, the chemical fungicides reduce the growth of the plant pathogenic fungus, and thus will allow for a prolonged opportunity for the *Cladosporium* to achieve its effect. It is thus submitted that a combination of the isolates of the present invention with suitable chemical fungicides will synergistically inhibit the fungal foliar pathogen thereby exceeding beyond a simple addition of the individual effects. Also a combination of the isolates of the invention with any other microbial fungal foliar pathogen antagonist will be useful in the present invention.

Another embodiment of the invention is a method to control a fungal pathogen on leaves, fruits and ears, comprising treating said plants with a composition according to the invention.

In such a method plants are sprayed with a composition according to the invention before or after an infection with the plant foliar pathogen. Spraying before infection will be useful to prevent an infection. Although, if the spores of the isolates are not completely viable, such anaphylactic spraying should be repeated regularly. If the spores are sufficiently viable, the

*Cladosporium* isolate will be able to grow in the phyllosphere of the plant, thus providing a long-lasting protection by preventing infections and reducing pathogen sporulation, thus slowing down epidemics. Furthermore, the *Cladosporium* isolate will reduce ascospore production in overwintering apple leaves and of spores of other plant pathogens in their residues which will result in less disease in the following season.

Once an infection has occurred, spraying should be performed regularly in order to effective control the disease.

Treatment with a composition according to the invention can be done both pre-harvest, i.e. when the fruits are still on the plant, but also post-harvest. It is shown in the experimental part that also post-harvest treatment is effective to combat fungal infections.

Yet another embodiment of the invention is the use of a *Cladosporium* strain according to the invention, or a composition according to the invention for the prevention or treatment of infection by a fungal foliar pathogen.

A further embodiment of the present invention is a *Cladosporium* strain as identified above, or a composition according to the invention for use in the control of a fungal foliar pathogen infection.

EXAMPLES

Example 1

In Vitro and Field Tests 2006

Material and Methods

Collection of Candidate Antagonists

Scab infected apples leaves were collected in September 2004 at 216 locations in The Netherlands, Belgium, and northwest and central Germany. Sampling locations were recorded by GPS. Most samples, consisting of 10-50 leaves, originated from old standard tress or abandoned orchards without any cropping management. From each sample, green leaves with sporulating colonies of *V. inaequalis* were incubated for 3 days at 20° C. in moist chambers. Thereafter, *V. inaequalis* colonies were visually inspected at 10 to 60× magnification for development of fungi different from *V. inaequalis*. Fungal mycelium or spores were isolated from the aerial parts of the colony with a sterile needle and transferred to oat meal agar (20 g oat meal, 15 g agar, 1000 ml tap water) and V8 agar (200 ml V8 juice, 3 g $CaCO_3$, 20 g agar, 1000 ml tap water), both containing 100 mg $l^{-1}$ streptomycine and 15 mg $l^{-1}$ tetracycline. Pure cultures were prepared from the developing colonies.

Pre-Screening of Candidate Antagonists

A rapid throughput system was used for a first check of candidate antagonists regarding their potential risks and economical feasibility of the development of a biocontrol product. Fungi belonging to the genera *Aspergillus, Penicillium* or *Fusarium* were discarded because of the potential of various species within these genera to produce mycotoxins. The remaining isolates of hyphal fungi were cultured in Petri dishes on oat meal agar for 21 days at 18° C. and 12 h per day blacklight; yeasts were cultured on basal yeast agar (10 g bacteriological peptone, 1 g yeast extract, 20 g glucose, 20 g agar, 1000 ml tap water) for 5 days at 18° C. For each isolate, the production of spores or yeast cells per plate was determined with the aid of a haemocytometer after preparation of suspensions using sterile tap water containing 0.01% Tween 80. Isolates producing less than $1\times10^5$ spores or yeast cells per plate were discarded. Ten μl of the suspensions were plated in duplicate in sterile wells, 16 mm in diameter containing 1.5 ml malt agar (1 g malt extract, 15 g agar, 1000 ml tap water). Different plates with inoculated wells were incubated at 5, 18 and 36° C. in the dark for 14 days. An additional plate with wells containing malt agar adjusted to approximately −10 and −7 MPa by adding $KCl_2$ were incubated at 18° C. for 14 days. Wells were inspected for fungal growth and fungi producing colonies at 36° C. and those not producing colonies at 5° C. or at −10 or −7 MPa were discarded. Remaining isolates were stored on potatoe dextrose agar (Oxoid, 39 g, 1000 ml tap water) at 4° C. until further use.

Production of Fungal Inocula

Conidia of the monospore isolate MB 363B of *V. inaequalis* obtained from M. Bengtsson, Royal Veterinary and Agricultural University, Frederiksberg C, Denmark, were produced following the method of Williams (1976). Duran bottles (500 ml) with 40 ml potato dextrose broth (24 g $l^{-1}$) and a wick of cheese cloth sized 10×25 cm spread on the inner surface of the bottle, the lower part touching the medium, were autoclaved and inoculated with 250 l of a suspension of mycelial fragments of *V. inaequalis*, prepared by flooding a culture of the fungus grown on potatoe dextrose agar with sterile water and gently rubbing with a sterile rubber spatula. Inoculated bottles were incubated at 18° C. in the dark. During the first 4 days, bottles were incubated at horizontal position so that most of the wick was covered by the broth, thereafter bottles were incubated in an upright position. Bottles were carefully rolled at day 2, 7 and 11 to distribute the broth with growing mycelium on the entire surface of the wick. After 14 days, the nutrient broth was decanted and 200 ml sterile tap water was added and the bottles were shaken thoroughly by hand for several minutes. The resulting conidial suspension was filtered through sterile nylon gauze with a mesh of 200 m and centrifuged at 5800 g for 30 min at 6° C. The pellet with conidia was re-suspended in tap water; the conidial concentration was determined with the aid of a haemocytometer and adjusted to $5\times10^5$ spores $ml^{-1}$ by adding sterile tap water. The suspension was stored at −18° C. until use. The yield was approximately $3\times10^6$ conidia per bottle.

For the screening experiments, candidate isolates of hyphal fungi were grown on oat meal agar for 28 days at 18° C. and 12 h blacklight per day; yeasts were grown on basal yeast agar for 5 days at 18° C. Suspensions of spores or yeast cells were prepared by flooding cultures with sterile tap water containing 0.01% Tween 80, gently rubbing with a sterile rubber spatula and filtration through sterile nylon gauze with a mesh of 200 m. Concentrations of the suspensions were determined with the aid of a haemocytometer and concentrations were adjusted to $1\times10^6$ spores or cell $ml^{-1}$ by adding sterile tap water containing 0.01% Tween 80.

For applications in the orchards, fungi were produced in the same way but concentrations were adjusted to $2\times10^6$ spores $ml^{-1}$. Conidia of 2 isolates were also produced in a fermenter, dried and formulated as wettable powder and stored at 5° C. Viability of dried conidia was determined before the beginning of the field experiments on agar. The concentration of conidial suspensions was adjusted to $2\times10^6$ viable conidia $ml^{-1}$. Viability of spores in the suspensions applied to the field was always checked again by spraying suspension on malt extract agar (1 g malt extract per liter) amended with tetracycline at 15 mg $l^{-1}$ and streptomycine at 100 mg $l^{-1}$ in the orchard and assessing the percentage of germinated spores after incubation at 20° C. for 24 h.

Seedling Assay

Seeds of apple cv Golden Delicious (G. J. Steingaesser & Comp. GmbH, Miltenberg, Germany) were seeded in moist sand and stratified at 4° C. for 6 weeks in the dark. Thereafter, seeds were further grown in the moist sand at room temperature and daylight. After approximately 14 days, young seedlings were transplanted into potting soil, one seedling per pot (6 cm square, 8 cm height). Seedlings were grown for 28 days with cycles of 16 h light at 18° C. and 8 h dark at 12° C. Plants used in experiments had at least 4 fully expanded leaves.

Seedlings were sprayed with conidial suspensions of *V. inaequalis* ($1\times10^5$ ml$^{-1}$) until run-off and placed in a moist chamber consisting of a plastic trays closed by a transparent plastic top. After 2 days incubation at 15° C. with diffuse light, tops were removed from the trays and seedlings further incubated for 3 or 4 days at 85% RH, 15° C. and 16 h light per day. Thereafter, *V. inaequalis*-inoculated seedlings were sprayed with suspensions of the above found isolates or water containing 0.01% Tween 80 as control. Two seedlings were used for each replicate of each treatment. The sets of 2 inoculated seedlings were placed in a polyethylene tent in a block design with 6 blocks (replicates) and complete randomization within blocks. Touching of leaves of neighbouring plants or the polyethylene was avoided. Seedlings were grown for 9 to 12 days at 15° C., with 16 h light per day at 138 E s$^{-1}$ m$^{-2}$. From both seedlings of each replicate, the lowest 5 true leaves (experiments 1-5) or the youngest just unfolded leaf at the beginning of the experiment (labelled with a metal ring; 'young leaves') and the 3 next elder leaves (experiments 6-14; 'old leaves') were carefully removed. Leaves of each replicate set of leaves were pooled, put into Duran bottles (100 ml) containing 15 ml of tap water with 0.01% Tween 80 for samples containing 2 youngest leaves or 30 ml for samples of containing 10 (exp 1-5) or 6 (experiments 6-14) leaves. Bottles were shaken with a flask shaker at 700 OCS min$^{-1}$.

Concentration of conidia of *V. inaequalis* was determined for each suspension with the aid of a haemocytometer. Leaf surfaces of each replicate set of leaves were measured with an area meter (Li-COR Biosciences, model 3100, Lincoln, U.S.A.).

Orchard Assay

Several rows of var. Jonagold within an organically managed orchard at Randwijk, The Netherlands, were pruned during spring and summer 2006 so that trees produced new shoots with young leaves highly susceptible for *V. inaequalis*. Depending on tree development and growth conditions for the trees pruning was carried out approximately 3 to 5 weeks before a set of trees was used for an experiment. Also the majority of young fruits were removed from the trees to stimulate the development of new shoots. Trees used for experiments in early summer (experiments 1 to 4) were not treated for scab control in 2006. Trees used in later experiments after half of July were treated with a sulphur schedule as common for the organic orchard in the early season to slow down the scab epidemic but remained untreated at least 3 weeks before and during the experiments.

A series of 8 experiments was carried out, each on a different set of trees. For each experiment 2 to 6 trees, depending on the number of newly produced shoots per tree, were chosen for each of 6 blocks (replicates). Within each block, 7 treatments were carried out. For each treatment (per replicate) 3 shoots were used which were produced on the same branch. Shoots were labelled with coloured metal rings so that the 2 youngest leaves fully expanded at the day of the first treatment could later be distinguished from the other leaves of the shoot. Treatments consisted of spraying tap water containing 0.01% Tween 80 as control, or suspensions of freshly produced spores of the antagonist *C. cladosporioides* H39. Separate treatments were carried out with fermenter-produced spores formulated as dry powders and resuspended in tap water containing 0.01% TWEEN 80. Spray applications were done using a compressed air-driven knapsack sprayer at 250 kPa until run-off. The different experiments were carried out in the period between 22 Jun. and 28 Sep. 2006. Experiments started with the first treatment 1 to 3 days after an infection period for *V. inaequalis* had been predicted according to the Mills table based on leaf wetness duration and temperature. Starting dates for the 8 experiments were 22 Jun., 29 Jun., 6 Jul., 31 Jul., 3 Aug., 7 Aug., 21 Aug., 24 Aug., and 24 Aug. 2006. In experiment 8 the period between expected infection period and first application was prolonged to 10 days, but leaves were labelled already 1 to 3 days after the expected infection period as in the other experiments. During all experiments, subsequent treatments were carried out at 3 to 4 day intervals. In the first 3 experiment, leaves were sampled 18 days after the first treatment (and thus 19 to 21 days after an expected infection period). In experiments 4 to 7, leaves were sampled 24 to 25 days after the first treatment (and thus 25 to 28 days after an expected infection period) to increase the time period for *V. inaequalis* sporulation and for possible antagonistic interactions. In experiment 8, leaves were sampled 24 days after the first application and thus 34 days after the expected infection period.

In each experiment, the 2 youngest leaves fully expanded at the beginning at the experiment together with the 2 next younger leaves (expanded during the course of the experiments) were pooled for the 3 shoots belonging to the same replicate so that a sample consisted of 12 leaves (young leaves'). From the same shoot, the next elder 3 to 12 leaves, depending on shoot size, were also sampled and pooled so that samples consisted of 9 to 36 leaves (elder leaves'). The average number of elder leaves sampled in the different experiments was 21.8. Samples of young leaves were put into 250-ml glass bottles. Within 2 h, 100-150 ml (depending on amount of leaves) of tap water with 0.01% Tween 80 was added and bottles were shaken with a flask shaker at 700 OCS min$^{-1}$ for 10 min. Samples of older leaves were processed in the same way using 1000-ml plastic bottles with 150-350 ml (depending on number of leaves) of tap water added before shaking. From the obtained suspensions, sub-samples of 6 ml were stored at −18° C. The concentration of conidia of *V. inaequalis* was determined for each suspension with the aid of a haemocytometer. The leaf surface of all leaves per sample was measured with an area meter.

Statistics

The number of *V. inaequalis* conidia produced cm$^{-2}$ leaf was calculated per replicate. If no conidia were detected, a detection limit was set at one conidium counted in the conidial suspension, resulting in an average detection limit for the various experiments of approximately 100 conidia cm$^{-2}$, e.g. ranging, depending on the leaf surfaces for the various replicates, between 74 and 212 cm$^{-2}$ for the first 3 experiments conducted under controlled conditions. Data obtained for 2 different leaf ages were natural logarithmic-transformed and analysed separately per leaf age by ANOVA. Experiments conducted under controlled conditions were analysed separately by comparing means of the control treatments and the individual antagonist treatments using unprotected LSD-tests (=0.05). Since P-values of ANOVAs often were greater than P=0.05, no further multiple comparisons between antagonist treatments were made (Ott and Longnecker, 2001). For the field experiments, natural logarithmic-transformed data obtained for 2 different leaf ages were analysed separately per leaf age by ANOVA with a block design, with individual experiments considered as main blocks and treatments were randomized within the 6 replicate blocks of each experiment. Statistically significant treatment effects (protected LSD-tests; =0.05) were indicated.

Results
Isolation of Fungi from *V. Inaequalis* Colonies and Pre-Screening

Growth of fungi different from *V. inaequalis* was frequently observed in sporulating colonies of the pathogen and several hundreds of fungal isolates were obtained. Isolates were grouped according to colony appearance and in total 148 isolates representing various colony types were tested in the pre-screening. 131 out of the 148 isolates produced more than $1 \times 10^5$ spores or yeast cells per plate and grown at different temperatures and water potentials. From these remaining 131 isolates, all were able to grow at 5° C.; 16 did not grow at −10 MP. 14 grew at 36° C. of which 1 isolate did not grow at WP=−10 MPa. Since many of such isolates with the preferred combination of characteristics belonged to *Cladosporium* spp., only a sub-set of randomly chosen isolates of this group was tested on seedlings. In total, 63 out of the 102 isolates were further tested in bio assays on apple seedlings.

Seedlings Tests

Fourteen experiments on seedlings were carried out. In the control treatments of the first 5 experiments, the conidia production on the five youngest leaves of the seedling was on average 3596 conidia $cm^{-2}$ and ranged for the different experiments between 1339 and 10509 conidia $cm^{-2}$ (back-transformed values). Since conidia production was high on the youngest leaf and much less on the elder leaves it was decided to sample such leaves separately in the subsequent experiments. In experiment 6-14, average conidiation on the young leaf was 2896 conidia $cm^{-2}$ and ranged for the different experiments between 728 and 6186 conidia $cm^{-2}$ (backtransformed values). For elder leaves, average conidiation was 453 conidia $cm^{-2}$ and ranged for the different experiments between 144 and 1313 conidia $cm^{-2}$ (backtransformed values). Variation in conidiation was not only high between experiments but also within experiments between sets of replicate seedlings.

Most of the 80 candidate isolates tested on seedlings did not statistically significantly reduce conidiation of *V. inaequalis*. One isolate, *C. cladosporioides* H39 caused a significant reduction of *V. inaequalis* on the young or elder leaves which could be repeated in subsequent independent experiments. However, efficacies (calculated on base of back-transformed values for young leaves) of this antagonist varied between 55 to 79% for *C. cladosporioides* H39 in the experiments in which it was tested and conidiation reduction was in some cases not statistically significant (Table 1). A few more isolates showed a strong statistically significant antagonistic effect in one experiment but such effects could not be repeated. Such isolates belonged to *A. pullulans, C. cladosporioides, P. pinodella*, and *Cladosporium* spp. In no case significant enhancements of conidiation of *V. inaequalis* after application of candidate isolates was observed.

Orchard Testing 2006

Apple scab developed moderately in the orchard before the first experiment started at 22 June. In June and first half of July, dry conditions accompanied with day temperatures often above 30° C. were not favourable for further apple scab development. Thereafter, rainy and cold weather was strongly favourable for apple scab until the end of the experiments.

During the first 3 experiments conducted under dry and warm conditions, 2.1 to 12.8×1000 conidia $cm^{-2}$ (backtransformed values) were found on young leaves and 9.5 to 40.3× 1000 conidia $cm^{-2}$ on elder leaves on water treated control plots (Table 2 A, B). After weather had changed to moist and cold conditions half of July, 46.3×1000 conidia $cm^{-2}$ on young leaves and 9.8×1000 conidia $cm^{-2}$ were found on leaves from control treatments in experiment 4. During the subsequent experiments conidia numbers increased to 227.3× 1000 conidia $cm^{-2}$ on young leaves and 132.1 conidia $cm^{-2}$ on elder leaves in experiment 8.

Viability of spores applied at the 25 application dates during the course of the series of experiments was assessed for each suspension on one agar plate sprayed in the field. Viability of *Cladosporium* sp. H39 was 92% (ranging from 82 to 99%). Formulated spores of *C. cladosporioides* H39 had a viability of approximately 47% at the beginning of the experiments. When spore suspensions were prepared for field applications, formulated spores of *C. cladosporioides* H39 formed clusters consisting of approximately 5 to 50 spores in the spraying suspensions so that a precise determination of spore germination was not possible. The majority of clusters of suspensions sprayed in the 11 applications showed fungal growth. Only few spore clusters applied between 10 August and 29 August showed fungal growth. It can be assumed that stored formulated spores had been used which lost their vigour during storage for the last treatments during experiment 4 and all treatments during experiments 5 and 6. From end of August onwards, a new batch of formulated spores was used of which the majority of spore clusters showed fungal growth. No significant treatments effects were found when data were analysed for each experiment separately. For an overall analysis, experiments 1, 5 and 6 were excluded because viable formulated *C. cladosporioides* H39 was not available during experiment 1 and viability was low during these experiments 5 and 6. A significant reduction of the number of conidia $cm^{-2}$ was found for treatments with formulated *C. cladosporioides* H39 on both young and elder leaves (Table 2 B). On average, conidia production was reduced by 42% on young and 38% on elder leaves. Such a trend was found during the first 3 experiments conducted under low disease pressure as well as during the last 2 experiments conducted under extremely high disease pressure. The nonformulated spores of the isolate did not reduce conidiation of *V. inaequalis*. When the formulation of *C. cladosporioides* H39 was applied containing only a few or even no living conidia, during experiments 5 and 6, no trend was found that the formulation itself had any reducing effect on conidiation (Table 2 A).

Example 2

Orchard Test 2007

Material and Methods
Fungal Inoculum

*Cladosporium cladosporioides* H39 was produced as in Example 1. The formulated product contained $2.0 \times 10^9$ spores $g^{-1}$ with a viability of 20%. During the experiment, the batch of formulated H39 was stored at 4° C. in the dark in plastic bags. Suspensions were made by adding the formulated granules to Tween water (0.01%) and stirring without any further pre-treatments. The final concentration was $1 \times 10^7$ spores $ml^{-1}$, equivalent to $2 \times 10^6$ viable spores $ml^{-1}$.

Spores of *Cladosporium cladosporioides* R406 were produced in Petri dishes on oat meal agar (20 g oat meal, 15 g agar, 1000 ml tap water) at 20° C. with 12 hrs blacklight per day. After 2 weeks of incubation, spores were suspended in tap water containing 0.01% Tween 80 and added to the plates. The suspension was filtered through gauze (200 m mesh) to remove mycelial cells and the number of spores was counted using a haemocytometer. Spore yields were $8-30 \times 10^8$ spores per agar plate (90 mm diameter) with an average viability of 93%, ranging between 73 to 97% for suspensions prepared at different dates. Viability of spores in the suspensions applied to the field was always checked by spraying suspension on malt extract agar (1 g malt extract, 15 g agar 1000 ml tap water, amended with tetracycline at 15 mg l$^{-1}$ and streptomycine at 100 mg l$^{-1}$) in the orchard and assessing the percentage of germinated spores after incubation at 18° C. for 24 h.
Orchard The experiment was carried out in 3 rows of var. Jonagold within an organically managed orchard at Randwijk, the Netherlands. The aim of the experiment was to control the summer epidemic of *Venturia inaequalis* (Vi) by antagonist applications starting end of June. Therefore it was essential to allow an initiation of a mild to moderate epidemic in the orchards during the primary season. The timing of sulphur applications was foreseen in a way that primary infections by ascospores could occur but progression of the epidemic could be controlled. No applications of sulphur were planned later than end of May. Unusual weather conditions during the primary season of 2007 with a period of 4 weeks without any rain were very unfavourable for Vi ascospore release and infection. After weather became more conducive after April, a mild apple scab epidemic developed until beginning of the experiment. No sulphur treatments were carried out to reduce the progression of the epidemic.

Experimental Design, Treatments and Assessments

The experiment was carried out in a design with 6 blocks, with 2 blocks in each of the 3 tree rows. Each block consisted of 4 plots, each with 4 trees. Between plots, 2 untreated trees served as buffer. The different treatments were randomly allocated to such plots. It was planned to spray the 4 trees of each plot at a rate of 2 l per plot twice per week with the following treatments: (1) tap water amended with Tween 80 (0.01%) as control; (2) suspension of formulated H39 ($2\times10^6$ spores ml$^{-1}$); (3) suspension of formulated R406 ($2\times10^6$ spores ml$^{-1}$). Applications were carried out twice per week at 16 dates between 28 June and 20 August using a hand-held sprayer operating with compressed air (AZO, Edecon, Ede, The Netherlands) with a 2-m boom and one nozzle (Birchmeier helico saphir 1.2, 2F-0.6; pressure 250 kPa). Since formulated spores of R406 were not available at the beginning of the experiment, treatment (3) was carried out with spores produced freshly in the laboratory for each application. Applications of R406 twice per week started with a delay at 12 July so that this fungus was applied only at 12 dates. Because no sufficient spores could be produced, only selected and labelled twigs obtained multiple sprays instead of whole tree treatments.

Assessments
Conidia Production.

Conidia production was assessed on susceptible young leaves developed during the course of the experiment at 3 sampling dates for leaves treated with Tween-water as control, or conidial suspensions of H39 and for 2 sampling dates for R406. Sampling dates were chosen so that sets of susceptible leaves present during a predicted infection period were sampled approximately 5 weeks after the infection period. The Mills table based on leaf wetness duration and temperature was used to predict infection periods. For each sampling, the second youngest just unfolded leaf was labelled 1 to 3 days after a predicted infection period on a set of 3 twigs belonging to the same tree in each plot. After 5 weeks, the 2 leaves just unfolded at the date of labelling and the next 2 younger leaves, unfolded after labelling, were sampled resulting in a sample consisting of 12 leaves per plot. Leaf samples were put into 250-ml glass bottles. Within 2 h, 100-150 ml (depending on amount of leaves) of tap water with 0.01% Tween 80 was added and bottles were shaken with a flask shaker (Stuart Scientific SF1, UK) at 700 OCS min$^{-1}$ for 10 min. From the obtained suspensions, sub-samples of 6 ml were stored at −18° C. and the concentration of conidia of Vi was determined later for each suspension with the aid of a haemocytometer. The leaf surface of all leaves per sample was measured with an area meter (Li-COR Biosciences, model 3100, Lincoln, U.S.A.).

Sampling dates were 6 August (of leaves labelled at 2 July), 16 August (of leaves labelled at 12 July), and 20 August (of leaves labelled at 16 July).

Epiphytic and Endophytic Colonisation.

Twenty labelled leaves of trees treated with Tween-water (control) or spore suspensions of H39 and of twigs treated with spore suspensions of R406 were collected at 4 October from each plot. All sampled leaves had been developed on the trees during the period between 28 June and 20 August when the series spray applications had been carried out. It thus can be assumed that all leaves obtained one or several spore applications at young developmental stages.

From each leaf, one leaf disc (9 mm diameter) was cut using a corkbohrer. The resulting 20 leaf discs per sample were pooled in sterile 50-ml vials containing 10 ml of sterile Tween-water (0.01%) and vials were shaken using a flask shaker at high speed (700 OCS min$^{-1}$) for 10 min. From the resulting suspensions, serial dilutions (1:10) were prepared and 100 l of undiluted and diluted suspensions were plated on each of 2 agar plates containing malt agar (10 g malt extract, 15 g agar, 1000 ml tap water) amended with 100 mg l$^{-1}$ streptomycine and 15 mg l$^{-1}$ tetracycline. Plates were incubated at 20° C. in the dark and colonies of *Cladosporium* spp., other hyphal fungi and yeasts were counted after 4, 7 and 11 days. From the colony counts, the number of colony forming units (CFU) cm$^{-2}$ leaf surface was calculated for each sample. After shaking of the leaf disks to remove epiphytically present fungi, the pooled 20 leaf disks per sample were surface-sterilised and homogenated in 5 ml sterile water using a mortar. For surface sterilisation, leaf discs were dipped in 96% ethanol followed by submersion for 1 minute in 0.5% sodium hypochlorite and subsequently rinsed 3 times with sterile water. From the resulting homogenates serial dilutions (1:10) were prepared in sterile water and 100 l of undiluted and diluted suspensions were plated on each of 2 malt agar plates containing 100 mg l$^{-1}$ streptomycine and 15 mg l$^{-1}$ tetracycline. Plates were incubated and colonies of endophytic fungi were assessed as described above.

Statistics

The number of Vi conidia produced per cm$^{-2}$ leaf surface was calculated per replicate sample. Natural logarithmic-transformed values of the control treatment were compared with the individual antagonist treatments separately for both leaf ages by one-sided unprotected LSD-test (=0.05). The logarithmic-transformed numbers of CFU per cm$^{-2}$ leaf surface were analysed by ANOVA followed by two-sided LSD-tests (=0.05).

Results

Weather conditions during the period of the experiments with frequent rainfalls and moderate temperatures were very favourable for apple scab. At the beginning of the experiments only light symptoms were present in the orchards. At the end heavy scab symptoms were observed on leaves of trees within the experimental plots and in the neighbourhood.

Spores of R406 produced freshly for each application date had high germination rates, generally above 80% (Table 3). Formulated spores of H39 germinated for 20-30% during the first weeks of the experiment but germination dropped to 4-16% for the last 4 treatments. The exceptional high value for spore germination of 76% at the first spraying date can be explained by experimental variation due to the small sample size of only 1 plate sprayed under orchard conditions.

On leaves sampled at 6 August, 16 August and 20 August from water-treated trees, 77,200 (13,900 to 139,800), 45,300 (35,200 to 55,200) and 32,200 (8,800 to 111,800) conidia $cm^{-2}$ were produced on average (backtransformed means, range for 6 replicates in brackets; FIG. 2). Variation between replicates thus was considerably high. On leaves of trees treated with H39, the number of spores was statistically significantly lower with 24,200 conidia $cm^{-2}$ (69% reduction) at the first sampling date and 22,000 conidia $cm^{-2}$ (51% reduction) at the second sampling date. For the last sampling date, no treatment effect was observed for H39. For the sampling dates when leaves treated with R406 were available, conidia counts at 16 August were 24,300 conidia $cm^{-2}$ for leaves treated with R406 resulting in a statistically significant reduction of conidia by 46%. For 20 August, only a reduction by 15% was observed and counts did not differ from the control treatment.

No treatment effects on leaf development or symptoms of phytotoxicity were observed.

Close to leaf fall, the endo- and epiphytical colonisation of leaves was assessed by plating leaf washings and homogenates of surface sterilised leaves on agar and counting of colony forming units (CFU). The endophytic colonisation by *Cladosporium* spp. was significantly higher and epiphytical colonisation by *Cladosporium* spp. tended to be higher for leaves which had been treated with H39 during summer. The endo- and epiphytical colonisation of H39-treated leaves by other hyphal fungi tended to be lower compared to untreated leaves. Epiphytical colonisation by yeasts was significantly lower for H39-treated leaves.

Example 3

Field Test 2005/2006

Materials and Methods
Experimental Design and Treatments

In autumn of 2005, 25 fungal isolates belonging to different species including *Cladosporium cladosporioides* R406 were applied on apple leaves from an organically managed orchard in Randwijk, the Netherlands, and treated leaves were placed on the orchard floor until next spring. The selection of candidates was based on the results of the pre-screening carried out on economical feasibility and possible risks (see example 1). Spores of isolate R406 were produced on oat meal agar (28 days incubation at 18° C.). Spore suspensions (500 ml per isolate) were prepared by flooding cultures on agar with sterile water containing 0.01% Tween 80. After gently rubbing with a rubber spatula to remove spores from fungal cultures, suspensions were filtered through sterile nylon gauze with a mesh of 200 m. Concentrations of suspensions were determined with the help of a haemocytometer and adjusted to $2\times10^6$ spores $ml^{-1}$. Spray applications were carried out using hand held sprayers operating with pressed air. Leaves of extension shoots were collected from the trees at 17 October to carry out the spray applications under controlled conditions in a glasshouse compartment. During the period between picking the leaves and fixing leaves in nettings again on the orchard floor, leaves were stored at 5° C. Leaves were fixed in nettings, each with 40 randomly chosen leaves, at 18 and 19 October. At 20 October 4 nettings with leaves per replicate of each treatment were sprayed with spore suspensions or water with approximately 20 ml of the suspensions (or water in the control treatments) at both sides. Two of the nettings, each containing 40 leaves, were destined for determination of the potential ascospore production of *V. inaequalis*, the other two nettings for determination of *V. inaequalis* population densities by TaqMan-PCR. After applications, leaves were dry again within approximately 30 min. Nettings with treated leaves were fixed on the orchard floor at 21 October on bare soil within the organic orchard at Randwijk. There were 6 blocks (replicates) in different rows of the orchard.

Each spore suspension was also sprayed on an agar plate (1/10 malt agar). Plates were incubated at 18° C. for 2 days and germination rate was determined. Spores of R406 had a viability of >90%.

Assessments

At 23, 24, 25, 30 and 31 Jan. 2006, respectively the nettings of the replicates 1 to 6 destined for the quantification of the *V. inaequalis* population densities by TaqMan-PCR were collected in the orchard, carefully rinsed with tap water to remove adhering soil and allowed to dry overnight at room temperature. Leaf residues of the 2 nettings per replicate of each treatment were removed from the nettings, cut in 1- to 2-cm pieces and a sample of 5-10 g was freeze dried and subsequently pulverized in a laboratory mill with a 1-mm mash sieve. Powdered samples were stored at –18° C. DNA was extracted and DNA of *V. inaequalis* was quantified by species-specific realtime PCR (TaqMan-PCR).

At 20 March (block A), 22 March (block B), 27 March (block C), 29 March (block D), 3 April (block E), and 5 April (block F), the nettings were collected in the orchard to quantify the potential ascospore production after ascospore extraction by bubbling air in water. Leaf residues of the 2 nettings per replicate of each treatment were air-dried (20° C., 70% RH, 2 days) and weight was determined. Subsequently, a sub-sample of maximum 7-17 g air-dried leaf residues of each sample was spread in a plastic tray on moist filter paper. Trays were covered by a plastic bag and leaf residues were incubated in these moist chambers for 7 days at 20° C. in the dark followed by 14 days at 20° C. with 12 h light per day to allow maturation (of a substantial fraction) of asci. Different climate rooms were used for incubation but leaves belonging to the same block were always incubated in the same room.

After incubation, leaf residues were transferred into 1000 ml-plastic bottles containing 150-350 ml water depending on the amount of leaf residues. Air (250 l per h) was bubbled through the water resulting in heavy turbulence during 2 h. Thereafter, the resulting suspension was passed through a sieve (1 mm mesh) to remove leaf debris. Two sub-samples (8 ml) of the suspension were stored at –20° C. Ascospore concentration in the suspensions was determined microscopically using a haemocytometer. Ascospore production was expressed as production per 80 leaves (originally fixed on the orchard floor in autumn) or per g air-dried leaf residue present at sampling date in spring. The ascospore production per 80 leaves is a result of the possible effect of the treatment on the decomposition and the ascospore production.

Statistics

Data obtained for ascospore numbers were logarithmic-transformed ($log_{10}$). All data were analysed by ANOVA. Means of the control treatments and the individual antagonist treatments were compared using LSD-tests (=0.05). Since P-values of ANOVAs often were greater than P=0.05, no further multiple comparisons between antagonist treatments were made.

Results

The amount of DNA of *V. inaequalis* was quantified in leaf residues sampled end of January 2006 by realtime PCR (TaqMan-PCR) using a species-specific primer pair and probe. The total amount of *V. inaequalis*-DNA in the total residues left from 80 leaves was calculated. Residues of leaves treated by *Cladosporium cladosporioides* R406 had significantly less *V. inaequalis*-DNA compared to the untreated control (Table 6).

The number of ascospores produced on leaves in spring was high with on average $7.5 \times 10^5$ (back-transformed values) for the residues of 80 leaves from the control treatment (Table 7). Per g leaf residue, $3.4 \times 10^4$ ascospores were produced in the control treatment (Table 8). For residues of leaves treated with isolate *Cladosporium cladosporioides* R406 ascospore counts were approximately 70% lower. These differences between control treatment and treatment with R406 were statistically significant for both the number of ascospores produced on the residues of 80 leaves and the number of ascospores produced per g of leaf residue (Tables 7 & 8). No other treatment with different candidate antagonists tended to cause a reduction of ascospores.

Example 4

Effect of *Cladosporium cladosporioides* H39 on Conidia Production of *Venturia inaequalis* Under Orchard Conditions Objective Applications of conidia of the antagonist *C. cladosporioides* H39, pilot-formulated as water dispersible granule (WG), reduced the conidia production of the apple scab pathogen *Venturia inaequalis* under orchard conditions in experiments carried out in 2006 and 2007 conditions (see Example 1 and 2). The objective of the experiment carried out in 2008 was to confirm these results in another season and to obtain first insight in the best timing of antagonist applications after predicted infection periods for *V. inaequalis*.

Production of Conidia of H39

For applications in the orchard, conidia of *C. cladosporioides* H39 were produced in a Solid—State Fermentation (SSF) system by PROPHYTA Biologischer Pflanzenschutz GmbH, Germany. The harvested conidia were formulated as a water dispersible granule (WG). For the preservation of product quality, the final product was stored at 4° C. Viability of dried conidia was determined on malt extract agar (1 g malt extract $l^{-1}$) before the beginning of the field experiment. Conidia incubated for 24 hours at 20° C. with germ tubes longer than half of the minimum diameter of a conidium were considered to be viable.

Orchard Assay

The experiment was carried out in the organically managed orchard at Applied Plant Research, Randwijk, The Netherlands on 8 years-old trees cv Jonagold. The aim of the experiment was to control the summer epidemic of apple scab by antagonist applications. Therefore it was essential to allow an initiation of an epidemic in the orchard during the primary season. Weather conditions during the primary season of 2008 favoured scab development and many scab symptoms were found in the orchard beginning of June. A severe hail event seriously damaged the orchard at June 22. At June 24 and 26, Topsin-M (a.i. 500 g thiophanate methyl $l^{-1}$, Certis Europe B. V., Maarsen, The Netherlands) was applied at of rate of 140 ml per 100 liter water (applied at 1000 l ha$^{-1}$) in the entire orchard and the neighbouring orchards to prevent wound infections by European fruit tree canker (*Nectria galligena*). No further fungicide treatments were carried out to reduce the progression of the scab epidemic before or during the experiment. During the following weeks, trees produced abundant new shoots with new leaves. Such newly formed leaves, not damaged by hail or reached by the fungicide sprays, were used in the experiment.

The experiment was arranged in a design with 6 blocks, with 2 blocks in the same tree row. Each block consisted of 3 plots, each with 4 trees. Between plots, 2 untreated trees served as buffer. The following 3 different treatments were randomly allocated to the plots: (1) untreated as control; (2) conidial suspension of formulated H39 ($2 \times 10^6$ viable conidia ml$^{-1}$; 2 l per plot). The spray additive Trifolio S-forte (Trifolio-M GmbH, Lahnau, Germany) was added to the suspension at a rate of 2 ml l$^{-1}$ to improve the spray layer on the leaf surface. Biweekly applications of H39 were carried out at July 22, July 24, July 28, July 31, August 5, August 7, August 11, and August 18. (3) The third treatment consisted of weekly application of sulphur (Thiovit-Jet, Syngenta Crop Protection B. V., Roosendaal, The Netherlands; a.i. 80% sulphur) at a rate of 0.4% (400 gram per 100 liter water at 1000 l ha$^{-1}$). Sulphur treatments were applied at July 22, July 28, August 5, and August 11.

The number of scabbed leaves and the number of scab spots per leaf were assessed for the leaves of 10 shoots of each of the 4 trees per plot before the experiment started at June 11. In total 227 to 239 leaves were examined per plot. At September 19, scab symptoms were assessed on 177 to 232 leaves per plot which had been produced after the beginning of the experiment. Disease severity (% leaf surface covered with scab symptoms) was estimated using following classes: 1: No scab; 2: 1-10% coverage; 3: 11-50% coverage; and 4: 51-100% coverage. A severity index was calculated using the formula:

$$DS=(0 \times N_1+1 \times N_2+2 \times N_3+3 \times N_4)/N_{total}*100$$

In which $N_1$, $N_2$, $N_3$, and $N_4$ is the number of leaves grouped in the classes 1, 2, 3, and 4, respectively, and $N_{total}$ is the total number of leaves assessed per plot.

Figure 3:
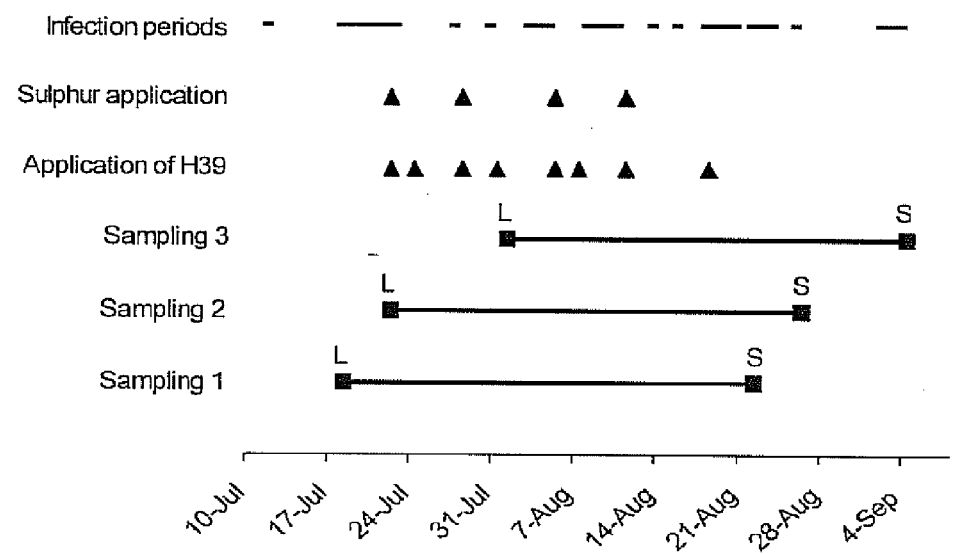

Conidia production of *V. inaequalis* was assessed on susceptible young leaves developed during the course of the experiment at 3 sampling dates. Sampling dates were chosen so that sets of susceptible leaves present during a predicted infection period were sampled approximately 5 weeks after the infection period. The Mills table based on leaf wetness duration and temperature was used to predict infection periods. The second youngest just unfolded leaf was labelled 1 to 3 days after a predicted infection period on a set of 3 twigs belonging to the same tree in each plot. The period between predicted infection infection and first application of *C. cladosporioides* H39 as well as the number of sprays and period of protection by sprays differed per sampling date (FIG. 3). After 35 days, the 2 leaves just unfolded at the date of labelling and the next 2 younger leaves, unfolded after labelling but expanded during the course of the experiment, were sampled resulting in a sample consisting of 12 leaves per plot. Sampling dates were August 22 (of leaves labelled on July 18), August 26 (of leaves labelled on July 22), and September 4 (of leaves labelled on August 1). The 12 leaves per sampled were pooled and put into 250-ml glass bottles. Within 2 h, 100-150 ml (depending on leaf mass) of tap water with 0.01% Tween 80 was added and bottles were shaken with a flask shaker at 700 OCS min$^{-1}$ for 10 min. From the obtained suspensions, sub-samples of 6 ml were stored at −18° C. The concentration of conidia of *V. inaequalis* was determined for each suspension with the aid of a haemocytometer. The leaf surface of all leaves per sample was measured with an area meter.

Results and Discussion

Conidia of *C. cladosporioides* H39 produced in spring 2008, formulated as a water dispersible granule following the pilot protocol and stored at 5° C. had a viability of 65% at the beginning of the experiments. Viability remained stable until the end of the experiment.

Before the experiment started, scab incidence on leaves did not differ for plots belonging to the different treatments. The mean incidence was 81.7% in plots used as control, 84.6% for plots later treated with H39, and 84.3% for plots later treated with sulphur. Also the number of leaf spots per leaf did not differ statistically, so that it can be assumed that the scab development was similar in the different plots before the experiment started.

Figure 4:
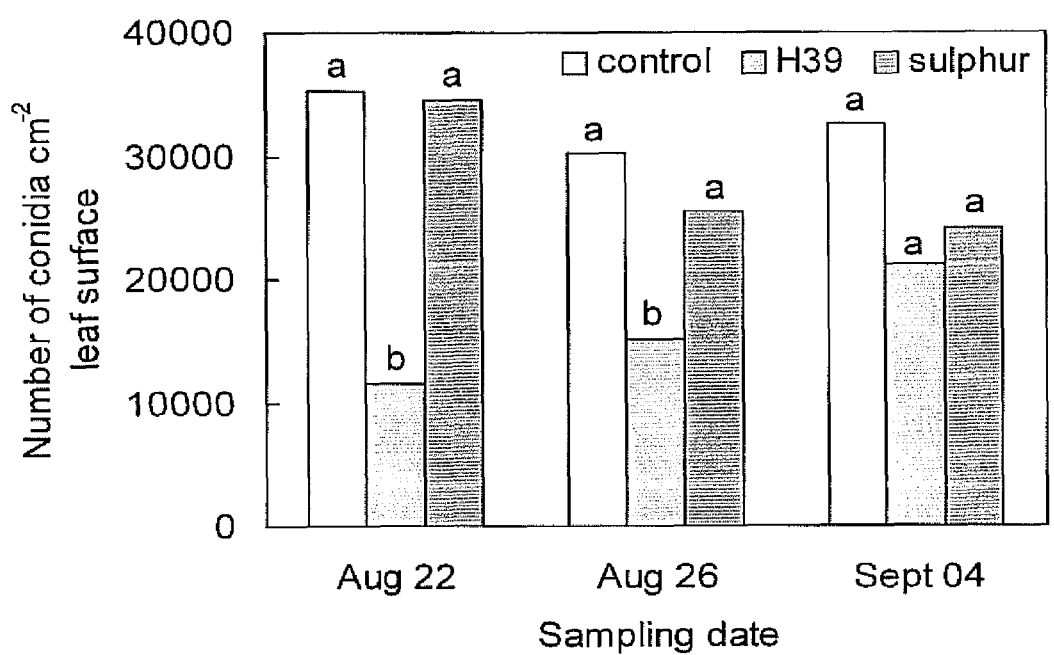
Figure 5:
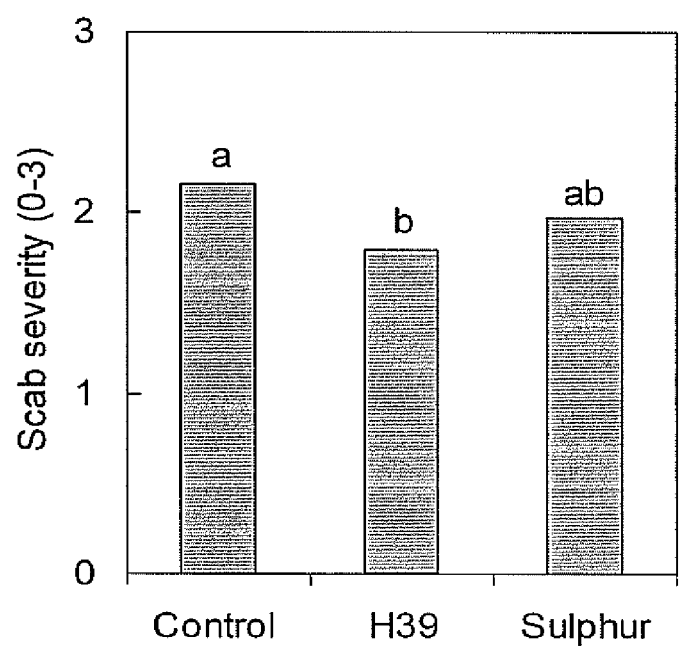

On leaves sampled on August 22, August 26 and September 4 from untreated trees 35,242 (11,447 to 74,870), 30,242 (18,926 to 59,497) and 32,533 (19,698 to 46,350) conidia of $V.$ $inaequalis\cdot cm^{-2}$ leaf surface were produced on average (backtransformed means, range for 6 replicates in brackets) (FIG. 4). On leaves of trees treated with $C.$ $cladosporioides$ H39, the number of spores was statistically significantly lower with 11,499 conidia of $V.$ $inaequalis\cdot cm^{-2}$ leaf surface (67% reduction based on backtransformed values) on the first sampling date and 15,139 conidia$\cdot cm^{-2}$ leaf surface (50% reduction) on the second sampling date. For the last sampling date, no significant effect was observed for applications of $C.$ $cladosporioides$ H39 with 21,163 conidia$\cdot cm^{-2}$ leaf surface (35% reduction) on treated leaves. Applications of sulphur resulted in a reduction of the number of conidia of $V.$ $inaequalis$ produced per $cm^2$ leaf surface by 2, 16, and 26% for the different sampling dates (FIG. 4). Scab severity, assessed at September 19, one month after the last treatment with H39, was 2.2 for the control treatment, but statistically significantly lower with 1.8 for H39-treated plots (FIG. 5). In sulphur treated plots, scab severity was 2.0 which did not differ significantly from the other treatments.

During the orchard experiment environmental conditions resulted in a high number of infection periods and scab development was favoured. Also the exceptional development of new shoots after the hail event supported the summer epidemic. Under such a severe disease pressure treatments with sulphur often are not sufficient to achieve disease control as also found in our experiment. Treatments with the antagonist H39 reduced conidia production of $V.$ $inaequalis$ under such severe conditions, confirming results from orchard experiments carried out in 2006 and 2007. The strongest effect was found for the first sampling date when treatments with H39 started after the predicted infection but were continued until 4 days before sampling. For the third sampling date, multiple treatments with H39 had been carried out already before the predicted infection period but the last treatment had been applied 17 days before sampling. In this situation, conidia production of $V.$ $inaequalis$ was reduced only by 35%. Since the effect of the antagonist may also depend on environmental factors which differed before the different sampling dates, more data are needed from repeated orchard experiments before conclusions on optimum timing of antagonist applications can be drawn.

For the first time also scab severity has been assessed after treatments with the antagonist H39. The reduced scab severity at the high scab level observed in the orchard demonstrated that $C.$ $cladosporioides$ H39 has a high potential to control scab epidemics.

Example 5

Orchard Assay in 2007/2008: Effect of Treatments with *Cladosporium cladosporioides* H39 and R406 During Summer on Ascospore Production of *Venturia inaequalis* on Treated Leaves after Overwintering Objective Treatments of apple leaves during summer with conidial suspensions of the antagonists *Cladosporium cladosporioides* H39 and R406 led to the reduction of conidia production of the scab fungus *Venturia inaequalis* on treated apple leaves under orchard conditions (see Example 1 and 2).

Objective of an additional assessment made on leaves treated in the orchard during the experiment in 2007 was to study the effect of such treatments of young developing leaves with the antagonists during summer on the ascospore production by $V.$ $inaequalis$ in treated leaves after overwintering.

Experimental Design.

The experiment was carried out in the organically managed orchard at Applied Plant Research, Randwijk, The Netherlands. The aim of the experiment was to assess the potential of antagonist applications to control the summer epidemic of apple scab and to reduce the inoculum load of $V.$ $inaequalis$ produced in overwintering apple leaves. Therefore it was essential to allow an initiation of a mild to moderate epidemic in the orchard during the primary season. Unusual weather conditions during the primary season of 2007 with a period of 4 weeks without any rain were very unfavourable for $V.$ $inaequalis$ ascospore release and infection. Weather became more conducive after April and a mild apple scab epidemic had developed when the first antagonist suspension was applied. No fungicide treatments were carried out to reduce the progression of the epidemic before or during the experiment.

The experiment was carried out on 8 year-old trees cv Jonagold in a design with 6 blocks, with 2 blocks in the same tree row. Each block consisted of 3 plots, each with 4 trees. Between plots, 2 untreated trees served as buffer. The 3 different treatments were randomly allocated to the plots. Trees were treated at a rate of 2 l per plot twice per week with the following treatments: (1) tap water amended with Tween 80 (0.01%) as control; and (2) conidial suspension of formulated H39 ($2\times10^6$ conidia $ml^{-1}$). Applications were carried out twice per week at 16 dates between 28 June and 20 August. (3) The third treatment consisted of multiple spray applications of conidial suspensions of $C.$ $cladosporioides$ R406. Conidia freshly produced at each application date were applied twice per week on the 4 trees of each replicate plot at 12 dates between 12 July and 20 August.

Conidia Production of $V.$ $inaequalis$ During Summer.

The effect of treatments on the conidia production of $V.$ $inaequalis$ has been reported as Example 2.

Ascospore Production of $V.$ $inaequalis$ in Overwintering Apple Leaves.

On 12 Jul. 2007 the second youngest just unfolded leaf was labelled on 25 twigs per plot. In some plots fewer twigs were available. On 4 Oct. 2007, leaves were sampled which had been just unfolded at the date of labelling and the next 2 younger leaves, unfolded after labelling. Depending on availability of leaves at the sampling date, 16 to 65 leaves per plot were collected. Sampled leaves of each plot were weighted and fixed between 2 iron nettings sized 50×50 cm (15×20 mm mesh) so that leaves did not touch each other. Nettings with leaves were placed on the orchard floor on bare soil within apple rows of the organic orchard at Randwijk and fixed with metal nails so that most of the netting surface touched the soil. There were 6 blocks (replicates) and nettings containing leaves from different treatments (applied during summer) were randomly distributed within blocks.

On 26 Feb. 2008, nettings were collected. Leaf residues of both nettings per replicate were pooled, air-dried (20° C., 70% RH, 2 days) and weighted. Subsequently, the air-dried leaf residues of each sample were spread in separate plastic trays (50×30×6 cm) on moist filter paper. Trays were covered by a plastic bag and leaf residues were incubated in these moist chambers for 7 days at 20° C. in the dark followed by 14 days at 20° C. with 12 h light (75 E) per day to allow maturation (of a substantial fraction) of asci. After incubation, leaf residues were transferred into 1000 ml-plastic bottles containing 150-350 ml water depending on the amount of leaf residues. Air ($250 l h^{-1}$) was bubbled through the water resulting in heavy turbulence during 2 h (Heye et al. 1981, Canadian Journal of Botany 59, 965-968; Philion, 1995, Msc Thesis McGill University, Montreal, Canada). Thereafter, the resulting suspension was passed through a sieve (1 mm mesh) to remove leaf debris. Two sub-samples (8 ml) of the suspension were stored at −20° C. Ascospore concentration in the suspensions was determined microscopically using a haemocytometer. Ascospore production was expressed as production per g leaves (originally fixed on the orchard floor in autumn) or per g air-dried leaf residue present at sampling date in spring.

Results and Discussion

On leaf residues from the control treatment, 220,089 ascospores were produced per g leaf residue (dry weight). This was equivalent to 37,171 ascospores produced per g leaf tissue (fresh weight) present in the preceding autumn (Table 9). In residues from leaves which had been treated with *C. cladosporioides* H39 in the preceding summer, only 109,044 ascospores were produced, equivalent to 15,733 ascospores produced per g leaf tissue (fresh weight) present in the preceding autumn. This reduction of ascospore production by 58% respectively 50% compared to the control treatment was statistically significant. The effect of *C. cladosporioides* R406 on ascospore production in spring after treatment of apple leaves during the preceding summer was less pronounced and not statistically significant.

It can be concluded that summer treatments of orchards during summer with the antagonist *C. cladosporioides* H39 and possibly also with *C. cladosporioides* R406 have a long-lasting effect in the following spring on the production of ascospores by *V. inaequalis*. A reduced number of ascospores produced on overwintering leaves will result in a lower inoculum pressure during the primary infection season of apple scab and thus a slower development of scab at the beginning of the epidemic. To our knowledge this is the first report demonstrating that treatments of young developing apple leaves, highly susceptible to scab, with an antagonist results in a significantly lower ascospore production on the treated leaves in the next season after overwintering.

Example 6

Effect of *Cladosporium cladosporioides* H39 on Spore Production of Various Pathogens Objective The objective of subsequent experiments was to evaluate the effect of the antagonist on various other plant pathogens.

Materials and Methods

Conidia of *Cladosporium cladosporioides* H39.

Conidia of *Cladosporium cladosporioides* H39 were produced in a Solid-State Fermentation (SSF) system by PROPHYTA Biologischer Pflanzenschutz GmbH, Germany. The harvested conidia were formulated as a water dispersible granule (WG). For preservation of the product quality, the final product was stored at −20° C. Viability of dried conidia was determined on malt extract agar (1 g malt extract $l^-$) before the beginning of the experiments. Conidia incubated for 24 hours at 20° C. with germ tubes longer than half of the minimum diameter of a conidium were considered to be viable. Sixty five percent of the conidia were viable.

Pathogens.

The following pathogen isolates were used in the study (with growth medium used for spore production in brackets): *Nectria galligena* 780 (oat meal agar; OA) causing canker in fruit trees and fruit rot, *Stemphylium versicarium* 850 (oat meal agar, OA) causing Brown Spot Disease and fruit rot in pear, *Botrytis aclada* 008 (OA) causing onion neck rot, *Botrytis cinerea* 143 (OA) causing grey mould in various crops, *Mycosphaerella fijiensis* 78 (potato dextrose agar; PDA), causing Black Sigatoka in banana, *Fusarium graminearum* 820 (PDA) causing *Fusarium* Head Blight in cereals, *Fusarium culmorum* 807 (PDA) causing *Fusarium* Head Blight in cereals, and *Alternaria brassicicola* 177 (PDA) causing diseases in *Brassiceae*. All fungi were incubated for 14 days at 24° C. with 12 hrs blacklight per day. To obtain spore suspensions, cultures were flooded with sterile tap water containing 0.01% Tween 80. After gently rubbing with a rubber spatula to remove spores from fungal cultures, suspensions were filtered through sterile nylon gauze with a mesh of 200 m. Concentrations of spore suspensions were determined with the aid of a haemocytometer and adjusted with sterile tap water containing 0.01% (v/v) Tween 80 to $1 \times 10^2$ spores $ml^{-1}$ and $1 \times 10^3$ spores $ml^{-1}$. For experiments with *Mycosphaerella fijiensis* also mycelial fragments, obtained after sterile grinding of the mycelial mass, were included in the suspensions. Only mycelial fragments with more than three cells were considered when the concentration of the suspensions was adjusted.

Experimental Design.

Separate experiments were carried out for each pathogen and substrate type and each experiment was repeated. Symptomless green leaves of pear, onion, rose, cyclamen, *Pelargonium*, banana and white cabbage were removed from greenhouse- or field-grown plants, and detached leaves were dried for several days at room temperature. Dry leaves were cut into segments each sized approximately 2×2 cm long, sealed in plastic bags and sterilised by gamma radiation of 40 kiloGray. Four-cm long segments of wheat straw (with 1 node) and of apple twigs (with 1 branch) were processed in the same way.

Segments of leaves, straw or twigs for use in bioassays were washed with sterile tap water to remove soluble nutrients. Therefore, approximately 80 segments of each substrate type were put in 150-ml aliquots of sterile tap water contained in sterile 250 ml-conical flasks over night at 4° C. Thereafter, segments were blotted dry with sterile filter paper. Four segments were placed in each of a series of moist chambers. Each chamber consisted of a sterile plastic petri dish (90 mm diameter) containing two sterile filter papers (85 mm diameter) and 6 ml sterile tap water. In each experiment five replications (petri dishes) for treatments with the antagonist *Cladosporium cladosporioides* H39 and five replications for the water control were applied at each of the two levels of pathogen application ($1 \times 10^2$ spores $ml^{-1}$ and $1 \times 10^3$ spores $ml^{-1}$). During the experiment, petri dishes were arranged in a completely randomised design.

Spore suspensions (or mycelial fragments in one case) of pathogens were sprayed on the segments of leaves, straw or twigs in the moist chambers. *Nectria galligena* was applied on apple twig segments, *Stemphylium vesicarium* on leaf segments of pear, *Botrytis aclada* on onion leaf segments, *Botrytis cinerea* on leaf segments of roses, cyclamen and *Pelargonium*, *Mycospharella fijiensis* on leaf segments of banana, *F. graminearum* and *F. culmorum* on straw segments, and *Alternaria brassicicola* on leaf segments of white cabbage. Treated tissue segments were incubated at 24° C. for 18 hrs. Immediately after the first incubation period, spore suspensions of *Cladosporium cladosporioides* H39 ($2 \times 10^6$ vital spores ml$^{-1}$), or water, were sprayed on the segments. The pathogens and antagonists were applied with sterile atomisers at approximately 5 l cm$^{-2}$ leaf segment. Thereafter, leaves were further incubated at 24° C. in the dark in the moist chambers. The straw segments with *F. graminearum* and *F. culmorum* were incubated from day 8 to day 13 with 12 hrs per day blacklight. Twigs with *Nectria galligena* were incubated from day 12 to day 14 with 12 hrs per day blacklight After a total incubation period of 9 days for *Botrytis aclada* and *Alternaria brassicicola* and 12 days for *Botrytis cinerea* (counted from the day on which pathogens were applied), the surface area of leaf segments covered with conidiophores of *Botrytis aclada, Botrytis cinerea* or *Alternaria brassicicola* was estimated using classes from zero to five, that represented, respectively, 0%, 1-5%, >5-25%, >25-50%, >50-75%, and >75-100% of the leaf surface covered with spore producing structures of the pathogens (Köhl et al. 1995, European Journal of Plant Pathology 101, 627-637). In the case of *Stemphylium vesicarium*, no conidiophores were produced, but the perfect stage (*Pleospora allii*) produced abundant pseudothecia. The coverage of the leaf surface with pseudothecia was estimated 16 days after inoculation using the same classes as for the coverage with conidiophores. From the number of leaf segments of each class ($n_{0-5}$) a sporulation index (SI) ranging from zero to hundred was calculated for each replication (petri dish) consisting of four leaf segments (SI=$(0 \times n_0 + 5 \times n_1 + 25 \times n_2 + 50 \times n_3 + 75 \times n_4 + 100 \times n_5)/4$). The number of colonies produced by *Mycosphaerella fijiensis* on banana leaf segments was counted after an incubation period of 15 days. The number of conidia of *F. graminearum* and *F. culmorum* produced on straw segments after 13 days was counted using a microscope. Therefore, straw segments from each petri dish were placed in an Erlenmeyer flask (100 ml) containing 10 ml of a washing liquid (20% ethanol in tap water containing 0.01% Tween 80). Flasks were shaken on a reciprocal shaker for 10 min, and the concentration of conidia in the suspensions was determined microscopically for *F. graminearum* and *F. culmorum* using a haemocytometer. The same method was used to quantify the number of conidia of *Nectria galligena* on apple twig segments after an incubation period of 14 days.

Statistics.

Data were analysed separately for each experiment by ANOVA followed by LSD-tests. If antagonist treatment x pathogen concentration interactions were not significant, the mean antagonist treatment effect is analysed as main effect. Data of spore counts were log-transformed before analysis: log-number of spores=$\log_{10}$(number of spores+0.01).

Results and Discussion

*Nectria galligena.*

A strong antagonistic effect of *Cladosporium cladosporioides* H39 was found against *Nectria galligena* causing canker in fruit trees and fruit rot. In orchards, the pathogen survives and multiplies on infected wound areas (cankers) of twigs (McCracken et al., 2003, Plant Pathology 52, 553-566). The inoculum produced in the bioassays on such tissues under controlled conditions was reduced by the antagonist by more than 99% (Table 10).

The results show that *Cladosporium cladosporioides* H39 has a high potential for use in biocontrol of fruit tree canker which is besides scab the most important disease in apple and pear production. Applications of the antagonist have thus the potential to control both major diseases, scab as well as fruit tree canker, in the major pome fruit crops.

*Stemphylium vesicarium.*

*Stemphylium vesicarium* is causing brown spot of pear in major pear production areas in Europe (Llorente & Montesi-nos, 2006). The major source of primary inoculum of the disease are overwintering necrotic pear leaves on which pseudothecia of the perfect stage (*Pleospora allii*) are produced.

Applications of *Cladosporium cladosporioides* H39 on necrotic leaves, pre-colonised by the pathogen, significantly reduced the formation of pseudothecia (estimated by assessment of leaf surface coverage by the fruiting bodies) in both experiments (Table 11). Biological control of brown spot by *Cladosporium cladosporioides* H39 may thus be achieved by applications of the antagonist to the canopy or on the orchard floor after leaf fall.

*Stemphylium vesicarium* was applied at a concentration of 1×10$^2$ spores ml$^{-1}$ and 1×10$^3$ spores ml$^{-1}$ 18 hrs before H39 was applied with 2×10$^6$ spores ml$^{-1}$.

[1] Mean of 5 replicates, each with 4 leaf segments; leaf surface coverage with pseudothecia was estimated.

[2] Significantly different from control treatment (LSD-test; =0.05).

*Botrytis* spp.

Presence of necrotic host tissues is a pre-requisite for epidemics of grey mould and other diseases caused by *Botrytis* spp. It has been demonstrated that competitive exclusion of *Botrytis* spp. from necrotic host tissues can be exploited for biocontrol of *Botrytis* incited diseases (Kohl et al., 2003, BioControl 48, 349-359).

*Cladosporium cladosporioides* H39 significantly reduced sporulation of *Botrytis aclada* and *Botrytis cinerea* in bioassays on tissues of all of the four different hosts tested (Tables 12-15). The antagonist has thus a potential for biological control of *Botrytis*—incited diseases in various crops.

*Mycosphaerella fijiensis.*

*Mycosphaerella fijiensis* is causing Black Sigatoka in banana (Arzanlou et al., 2007, Phytopathology 97, 1112-1118). The disease is the major threat in banana production. Disease control at present depends on multiple fungicide applications. The pathogen survives and multiplies in necrotic lesions on leaves.

The results of the bio-assay on necrotic banana leaves show that the antagonist *Cladosporium cladosporioides* H39 has a promising potential for biological control of the disease. Although spores were not formed by the pathogen under the experimental conditions, it clearly could be demonstrated that the antagonist is able to exclude the pathogen from substrate colonisation (Table 16).

*Fusarium graminearum* and *Fusarium culmorum.*

*Fusarium graminearum* and *Fusarium culmorum* are causing *Fusarium* Head Blight in cereals and maize. The disease is causing yield losses and, often more important, severe quality losses due to formation of mycotoxins by the pathogens. Straw stubbles and other debris are the main inoculum source of the disease (Osborne & Stein, 2007, International Journal of Food Microbiology 119, 103-108).

*Cladosporium cladosporioides* H39 significantly reduced conidia production of both *Fusarium* spp. on straw segments pre-colonised by the pathogens (Table 17 and 18) and thus has the potential for use in biocontrol of these major pathogens in cereal production.

*Alternaria brassicicola.*

Black leaf spot caused by *Alternaria brassicicola* is a major disease of *Brassiceae* in vegetable production. The pathogen sporulates within infected necrotic lesions and crops debris (Humpherson-Jones, 1989, Annals of Applied Biology 115, 45-50). Besides leaves, also whole seedlings as well as pods including developing seeds in seed production fields can be damaged.

A strong significant reduction of the conidia production of *Alternaria brassicicola* was found in the bio-assays after application of *Cladosporium cladosporioides* H39 to pre-colonised necrotic leaves of white cabbage (Table 19).

Example 7

Effect of *Cladosporium cladosporioides* H39 on Fruit Rot of Apple

Objective

The objective of a subsequent experiment was to evaluate the effect of the antagonist on *Monilia fructigena* causing post-harvest fruit rot on apple.

Material and Methods

Conidia of *Cladosporium cladosporioides* H39.

Conidia of *Cladosporium cladosporioides* H39 were produced as in Example 6.

Pathogen.

*Monilia fructigena* 1067, causing fruit rot in various fruit crops, was grown on oat meal agar for 14 days at 24° C. with 12 hrs blacklight per day. To obtain spore suspensions, cultures were flooded with sterile tap water containing 0.01% Tween 80. After gently rubbing with a rubber spatula to remove spores from fungal cultures, suspensions were filtered through sterile nylon gauze with a mesh of 200 m. Since sporulation was poor, also mycelial fragments, obtained after sterile grinding of the mycelial mass, were included in the suspensions. Only mycelial fragments with more than three cells were considered when the concentration of the suspensions was determined with the aid of a haemocytometer and adjusted with sterile tap water containing 0.01% (v/v) Tween 80 to $1 \times 10^2$ spores and mycelial fragments $ml^{-1}$ and $1 \times 10^3$ spores and mycelial fragments $ml^{-1}$.

Experimental Design.

Symptomless organically produced apples cv. Elstar were used in the bio-assays. Apples were surface-sterilised by submerging in 70% ethanol for 1 min and rinsed three-times in sterile tap-water. Four apples were placed into moist chambers (sized 28×15×9 cm; with moistened filter paper on bottom; enclosed by a lid) and two wounds (approximately 3 mm in diameter and 5 mm deep) were made using sterile cocktail pickers (Jijakli & Lepoivre, 1992, In: Fokkema, N.J., J. Köhl & Y. Elad, Biological control of foliar and post-harvest diseases, IOBC/WPRS Bulletin Vol. 16(11), pp. 106-110.). Fifty l of sterile water were applied to wounds of the control treatments. In another treatment, 50 l of a conidial suspension of *Cladosporium cladosporioides* H39 ($2 \times 10^6$ vital spores $ml^{-1}$) were added to each wound. Treated apples were incubated at 24° C. for 24 hrs. Subsequently, apples were treated with suspensions of spores and mycelial fragments of *Monilia fructigena* at $1 \times 10^2$ and $1 \times 10^3$ spores and mycelial fragments and were further incubated in the moist chambers at 24° C. Each treatment was carried out in 5 replicates, each replicate consisting of 4 apples in the same moist chamber, and moist chambers with various treatments were arranged in a completely randomised design. The experiment was repeated twice. The diameter of lesions developed from the inoculated wounds was measured 8 and 12 days after application of *Monilia fructigena*.

Results and Discussion

*Monilia fructigena* caused severe fruit rot on wounds of apple fruits under the experimental conditions, e.g. lesions were produced in the control treatment of both experiments on all wounds at the high pathogen level. Application of conidia of *Cladosporium cladosporioides* H39 reduced the number of infected wounds in most cases (Table 20a). The average lesion size was reduced by antagonist treatments by up to 70% (Table 20b). On average, fruit rot (measured as lesion size) was statistically significantly reduced by 50% in the first experiment, and by 30% in the second experiment.

The results demonstrate that applications of *Cladosporium cladosporioides* H39 during the growing season have the potential to protect apple fruits from pre-harvest and post-harvest fruit rot caused by *Monilia fructigena*. Also post-harvest treatments with *Cladosporium cladosporioides* H39 are promising to protect fruit from post-harvest rot during storage.

TABLE 1

Effect of *Cladosporium cladosporioides* H39 on conidia production of *Venturia inaequalis* on apple seedlings under controlled conditions. In total, 63 fungal isolates were tested in 14 experiments. Only results of the promising isolate are presented.

Number of conidia $cm^{-2}$ [a]

| | Experiment | | | | | | |
|---|---|---|---|---|---|---|---|
| Treatment | 1 (n = 8) [b] | 3 (n = 9) | 9 (n = 10) | 10 (n = 10) | 11 (n = 10) | 13 (n = 10) | 14 (n = 11) |
| Number of treatments | 8 | 9 | 10 | 10 | 10 | 10 | 11 |
| Youngest leaves | | | | | | | |
| Control | 1339 | 4915 | 1960 | 2393 | 4188 | 728 | 1480 |
| C. cladosporioides H39 | — | — | — | — | 863* (79) | 330 (55) | 572 (61) |
| Elder leaves | | | | | | | |
| Control | — | — | 331 | 359 | 1313 | 144 | 614 |
| C. cladosporioides H39 | — | — | — | — | 354* (73) | 116 (19) | 162* (74) |

[a] Backtransformed values; efficacy relative to control treatment in brackets.

[b] Total number of treatments.

[c] Statistically different from the control treatment.

[d] Not tested.

In experiments 1 and 3, the 4 youngest leaves per seedling were pooled; in the other experiments, the youngest leaf was sampled separately from the 3 next eldest leaves.

TABLE 2A

Effect of applications of *Phoma pinodella* H3, *Coniothyrium cereale* H33, *Cladosporium* sp. H35 and *Cladosporium cladosporioides* H39 on conidia production of *Venturia inaequalis* under orchard conditions. Experiments 1, 5, and 6.
Ln-Number of conidia $cm^{-2}$

| Treatment | Experiment | | | |
|---|---|---|---|---|
| | 1 | 5 | 6 | Mean |
| Youngest leaves | | | | |
| Control | 9.5 (12.8) | 10.1 (24.9) | 9.8 (18.0) | 9.8 (18.0) |
| *C. cladosporioides* H39 | 9.1 (8.6) | 10.7 (46.1) | 10.7 (42.5) | 10.2 (26.9) |
| *C. cladosporioides* H39 formulated, low viability | — | 10.4 (32.4) | 10.4 (31.8) | 10.4 (32.9) |
| Elder leaves | | | | |
| Control | 9.2 (9.5) | 9.2 (9.6) | 9.3 (10.4) | 9.2 (9.9) |
| *C. cladosporioides* H39 | 9.5 (12.9) | 10.2 (26.1) | 9.7 (16.1) | 9.8 (18.0) |
| *C. cladosporioides* H39 formulated, low viability | — | 9.3 (11.0) | 9.7 (16.1) | 9.5 (13.3) |

[a] Backtransformed values × 1000 in brackets.

TABLE 2B

Effect of applications of *Phoma pinodella* H3, *Coniothyrium cereale* H33, *Cladosporium* sp. H35 and *Cladosporium cladosporioides* H39 on conidia production of *Venturia inaequalis* under orchard conditions. Experiments 2, 3, 4, 7, and 8.
Ln- Number of conidia $cm^{-2}$ [a]

| Treatment | Experiment | | | | | |
|---|---|---|---|---|---|---|
| | 2 | 3 | 4 | 7 | 8 | Mean |
| Youngest leaves | | | | | | |
| Control | 8.2 (3.6) | 7.6 (2.1) | 10.7 (46.3) | 11.8 (132.1) | 12.3 (227.3) | 10.1 (25.3) |
| *C. cladosporioides* H39 | 8.9 (6.9) | 7.9 (2.7) | 10.2 (25.8) | 12.4 (253.8) | 12.1 (183.8) | 10.3 (29.5) |
| *C. cladosporioides* H39 formulated | 7.4 (1.6) | 6.9 (0.9) | 10.4 (31.7) | 11.4 (90.4) | 11.9 (147.2) | 9.6* (14.6) |
| Elder leaves | | | | | | |
| Control | 10.6 (40.3) | 9.2 (12.3) | 9.2 (9.8) | 11.2 (72.8) | 11.8 (132.1) | 10.4 (33.0) |
| *C. cladosporioides* H39 | 10.5 (35.3) | 8.9 (7.5) | 8.7 (5.8) | 11.4 (93.4) | 11.9 (145.7) | 10.3 (27.6) |
| *C. cladosporioides* H39 formulated | 10.0 (21.3) | 8.6 (5.5) | 8.8 (6.6) | 10.9 (52.3) | 11.4 (90.7) | 9.9* (20.5) |

[a] Backtransformed values × 1000 in brackets.
[b] Statistically different from the control treatment

TABLE 3

Application dates and spore germination of applied inocula of H39 and R406 (as estimated from counting from 1 agar plate sprayed in the orchard).

| Date of application | Spore germination (%) | |
|---|---|---|
| | H39 | R406 |
| 28 June | 76 | — |
| 2 July | 26 | — |
| 5 July | 47 | — |
| 9 July | — | — |
| 12 July | 28 | 96 |
| 16 July | 32 | 97 |
| 19 July | 28 | 95 |
| 23 July | 19 | 97 |
| 26 July | 26 | 94 |
| 30 July | 23 | 96 |
| 2 August | 16 | 97 |
| 6 August | 11 | 90 |
| 9 August | 4 | 96 |
| 13 August | 4 | 95 |
| 16 August | 10 | 95 |
| 20 August | 4 | 73 |

TABLE 4

Epiphytical colonisation of apple leaves sampled at 4 Oct. 2007. Leaves had been treated twice per week from 28 June until 20 August with H39 and V301.61 (16 applications in total) or from 12 July until 20 August with R406 (12 applications in total).

| Treatment | Number of CFU cm$^{-2}$ leaf surface (backtransformed) | | |
|---|---|---|---|
| | *Cladosporium* spp. | Hyphal fungi different from *Cladosporium* spp. | Yeasts |
| Control | 1005 | 1285 | 397 a[1] |
| H39 | 2223 | 1042 | 152 b |
| R406 | 502 | 400 | 100 b |
| | ($F_{prob}$ = 0.076) | ($F_{prob}$ = 0.069) | |

[1] Values of the same column with common letters do not differ statistically significantly (LSD; = 0.05).

TABLE 5

Endophytical colonisation of apple leaves sampled at 4 Oct. 2007. Leaves had been treated twice per week from 28 June until 20 August with H39 and V301.61 (16 applications in total) or from 12 July until 20 August with R406 (12 applications in total).

| Treatment | Number of CFU cm$^{-2}$ leaf surface (backtransformed) | | |
|---|---|---|---|
| | *Cladosporium* spp. | Hyphal fungi different from *Cladosporium* spp. | Yeasts |
| Control | 1.19 b [1] | 4.97 | 1.95 |
| H39 | 1.66 a | 2.72 | 3.75 |
| R406 | 1.20 b | 2.93 | 1.99 |
| | | ($F_{prob}$ = 0.182) | ($F_{prob}$ = 0.171) |

[1] Values of the same column with common letters do not differ statistically significantly (LSD; = 0.05).

TABLE 6

Effect of spray applications of antagonist R406 on apple leaves in autumn 2005 on content of DNA of *V. inaequalis* in spring as determined by species-specific real-time PCR (TaqMan-PCR). Leaf residues were sampled on 23 to 31 Jan. 2006.

| Treatment | pg DNA of *V. inaequalis* | |
|---|---|---|
| | per mg dry weight of leaf residues | in residues of 80 leaves |
| Control | 372 | 10093 |
| R406 | 226 | 5007 *[1] |

[1] Statistically significantly different from the control treatment (LSD$_{5\%}$ = 5057).

TABLE 7

Effect of spray applications of antagonist R406 on apple leaves in autumn 2005 on *V. inaequalis* ascospore production on leaf residues of 80 leaves in spring 2006.

| Treatment | Number of ascospores per 80 leaves | | |
|---|---|---|---|
| | Log$_{10}$-transformed | Back-transformed | Relative to control [1] |
| Control | 5.88 | 749894 | 100 |
| R406 | 5.37 *[2] | 235505 | 31 |

[1] At back-transformed scale.
[2] Statistically significantly different from the control treatment (LSD$_{5\%}$ = 0.3604).

TABLE 8

Effect of spray applications of antagonist R406 on apple leaves in autumn 2005 on *V. inaequalis* ascospore production per gram of leaf residues in spring 2006.

| Treatment | Number of ascospores per g leaf residue | | |
|---|---|---|---|
| | Log$_{10}$-transformed | Back-transformed | Relative to control [1] |
| Control | 4.54 | 34316 | 100 |
| R406 | 4.07 *[2] | 11722 | 34 |

[1] At back-transformed scale.
[2] Statistically significantly different from the control treatment (LSD$_{5\%}$ = 0.3183).

TABLE 9

Effect of treatments of young leaves with *Cladosporium cladosporioides* H39 and R406 carried out during summer between June 28 and August 20 on ascospore production of *Venturia inaequalis* in treated leaves after overwintering on the orchard floor. Orchard experiment 2007/2008.

| Treatment | Log-Number of ascospores g$^{-1}$ of | |
|---|---|---|
| | original leaf sample (fresh weight) | leaf residues in spring (dry weight) |
| Control | 4.57 (37,171) [a] | 5.34 (220,089) |
| H39 | 4.20 *[b] (15,733) | 5.04 * (109,044) |
| R406 | 4.52 (32,991) | 5.32 (211,203) |

[a] Backtransformed values.
[b] Significantly different from control treatment (one-sided LSD-test; a = 0.05).

TABLE 10

Effect of *Cladosporium cladosporioides* H39 on sporulation of *Nectria galligena* on apple twig segments incubated in moist chamber at 24° C. for 14 days.

| Treatment | Log-number of conidia per straw segment [1] | | |
|---|---|---|---|
| | 1 × 10$^2$ spores ml$^{-1}$ | 1 × 10$^3$ spores ml$^{-1}$ | Mean |
| Experiment 1 | | | |
| Water control | 6.64 (4,365,200) | 6.56 (3,630,800) | 6.60 (3,981,100) |
| H39 | 3.76 (5,800) | 3.06 (1,100) | 3.41 *[2] (2,600) |
| Experiment 2 | | | |
| Water control | 6.59 (3,881,500) | 6.75 (562,300) | 6.67 (4,666,600) |
| H39 | 4.32 (20,900) | 4.44 (27,200) | 4.38 * (23,800) |

*Nectria galligena* was applied at a concentration of 1·10$^2$ spores ml$^{-1}$ and 1·10$^3$ spores ml$^{-1}$ 18 hrs before H39 was applied with 2 × 10$^6$ spores · ml$^{-1}$.
[1] Mean of 5 replicates, each with 4 twig segments; backtransformed values in brackets.
[2] Significantly different from control treatment (LSD-test; = 0.05).

TABLE 11

Effect of *Cladosporium cladosporioides* H39 on sporulation of *Pleospora allii* (*Stemphylium vesicarium*) on necrotic pear leaves incubated in moist chamber at 24° C. for 16 days.

| | Sporulation index of *Pleospora allii* [1] | | |
|---|---|---|---|
| Treatment | $1 \times 10^2$ spores ml$^{-1}$ | $1 \times 10^3$ spores ml$^{-1}$ | Mean |
| Experiment 1 | | | |
| Water control | 29.5 | 36.8 | 33.1 |
| H39 | 8.2 | 26.8 | 17.5 *[2] |
| Experiment 2 | | | |
| Water control | 49.0 | 48.8 | 48.9 |
| H39 | 11.5 | 18.2 | 14.9 *[2] |

TABLE 12

Effect of *Cladosporium cladosporioides* H39 on sporulation of *Botrytis aclada* on necrotic onion leaves incubated in moist chamber at 24° C. for 9 days.

| | Sporulation index of *Botrytis aclada* [1] | | |
|---|---|---|---|
| Treatment | $1 \times 10^2$ spores ml$^{-1}$ | $1 \times 10^3$ spores ml$^{-1}$ | Mean |
| Experiment 1 | | | |
| Water control | 93.8 | 98.8 | 96.2 |
| H39 | 10.0 | 12.0 | 11.0 *[2] |
| Experiment 2 | | | |
| Water control | 92.5 | 83.0 | 87.8 |
| H39 | 8.8 | 18.0 | 13.4 * |

*Botrytis aclada* was applied at a concentration of $1 \times 10^2$ spores ml$^{-1}$ and $1 \times 10^3$ spores ml$^{-1}$ 18 hrs before H39 was applied with $2 \times 10^6$ spores ml$^{-1}$.
[1] Mean of 5 replicates, each with 4 leaf segments.
[2] Significantly different from control treatment (LSD-test; = 0.05).

TABLE 13

Effect of *Cladosporium cladosporioides* H39 on sporulation of *Botrytis cinerea* on necrotic rose leaves incubated in moist chamber at 24° C. for 12 days.

| | Sporulation index of *Botrytis cinerea* [1] | | |
|---|---|---|---|
| Treatment | $1 \times 10^2$ spores ml$^{-1}$ | $1 \times 10^3$ spores ml$^{-1}$ | Mean |
| Experiment 1 | | | |
| Water control | 76.2 | 85.0 | 80.6 |
| H39 | 17.5 | 43.0 | 30.2 *[2] |
| Experiment 2 | | | |
| Water control | 61.5 | 96.2 | 78.9 |
| H39 | 35.8 | 85.0 | 60.4 * |

*Botrytis cinerea* was applied at a concentration of $1 \times 10^2$ spores ml$^{-1}$ and $1 \times 10^3$ spores ml$^{-1}$ 18 hrs before H39 was applied with $2 \times 10^6$ spores ml$^{-1}$.
[1] Mean of 5 replicates, each with 4 leaf segments.
[2] Significantly different from control treatment (LSD-test; = 0.05).

TABLE 14

Effect of *Cladosporium cladosporioides* H39 on sporulation of *Botrytis cinerea* on necrotic cyclamen leaves incubated in moist chamber at 24° C. for 12 days.

| | Sporulation index of *Botrytis cinerea* [1] | |
|---|---|---|
| Treatment | $1 \times 10^2$ spores ml$^{-1}$ | $1 \times 10^3$ spores ml$^{-1}$ |
| Experiment 1 | | |
| Water control | 95.0 | 95.0 |
| H39 | 28.2 *[2] | 66.5 * |
| Experiment 2 | | |
| Water control | 95.0 | 90.0 |
| H39 | 57.8 * | 95.5 |

*Botrytis cinerea* was applied at a concentration of $1 \times 10^2$ spores ml$^{-1}$ and $1 \times 10^3$ spores ml$^{-1}$ 18 hrs before H39 was applied with $2 \times 10^6$ spores ml$^{-1}$.
[1] Mean of 5 replicates, each with 4 leaf segments.
[2] Significantly different from control treatment (LSD-test; = 0.05).

TABLE 15

Effect of *Cladosporium cladosporioides* H39 on sporulation of *Botrytis cinerea* on necrotic *Pelargonium* leaves incubated in moist chamber at 24° C. for 12 days.

| | Sporulation index of *Botrytis cinerea* [1] | | |
|---|---|---|---|
| Treatment | $1 \times 10^2$ spores ml$^{-1}$ | $1 \times 10^3$ spores ml$^{-1}$ | Mean |
| Experiment 1 | | | |
| Water control | 34.8 | 42.0 | 38.4 |
| H39 | 1.5 | 8.5 | 5.0 *[2] |
| Experiment 2 | | | |
| Water control | 24.5 | 23.2 | 23.9 |
| H39 | 0.2 | 11.0 | 5.6 * |

*Botrytis cinerea* was applied at a concentration of $1 \times 10^2$ spores ml$^{-1}$ and $1 \times 10^3$ spores ml$^{-1}$ 18 hrs before H39 was applied with $2 \times 10^6$ spores ml$^{-1}$.
[1] Mean of 5 replicates, each with 4 leaf segments.
[2] Significantly different from control treatment (LSD-test; = 0.05).

TABLE 16

Effect of *Cladosporium cladosporioides* H39 on sporulation of *Mycosphaerella fijiensis* on necrotic banana leaves incubated in moist chamber at 24° C. for 15 days.

| Treatment | Number of colonies of *Mycosphaerella fijiensis* per leaf segment [1] |
|---|---|
| Experiment 1 | |
| Water control | 5.65 |
| H39 | 0.15 *[2] |
| Experiment 2 | |
| Water control | 10.15 |
| H39 | 0.00 * |

*Mycosphaerella fijiensis* was applied at a concentration of $1 \times 10^3$ mycelial fragments ml$^{-1}$ 18 hrs before H39 was applied with $2 \times 10^6$ spores ml$^{-1}$.
[1] Mean of 5 replicates, each with 4 leaf segments.
[2] Significantly different from control treatment (LSD-test; = 0.05).

TABLE 17

Effect of *Cladosporium cladosporioides* H39 on sporulation of *Fusarium graminearum* on wheat straw incubated in moist chamber at 24° C. for 13 days.

| | Log-number of conidia per straw segment [1] | |
|---|---|---|
| Treatment | $1 \times 10^2$ spores ml$^{-1}$ | $1 \times 10^3$ spores ml$^{-1}$ |
| | Experiment 1 | |
| Water control | 5.615 (412,100) | 5.731 (538,300) |
| H39 | 4.759 *[2] (57,400) | 5.501 (317,000) |
| | Experiment 2 | |
| Water control | 5.872 (744,700) | 5.885 (767,400) |
| H39 | 5.416 * (260,600) | 5.670 * (467,700) |

*Fusarium graminearum* was applied at a concentration of $1 \times 10^2$ spores ml$^{-1}$ and $1 \times 10^3$ spores ml$^{-1}$ 18 hrs before H39 was applied with $2 \times 10^6$ spores ml$^{-1}$.
[1] Mean of 5 replicates, each with 4 straw segments; backtransformed values in brackets.
[2] Significantly different from control treatment (LSD-test; = 0.05).

TABLE 18

Effect of *Cladosporium cladosporioides* H39 on sporulation of *Fusarium culmorum* on wheat straw incubated in moist chamber at 24° C. for 13 days.

| | Log-number of conidia per straw segment [1] | | |
|---|---|---|---|
| Treatment | $1 \times 10^2$ spores ml$^{-1}$ | $1 \times 10^3$ spores ml$^{-1}$ | Mean |
| | Experiment 1 | | |
| Water control | 6.496 (3,133,290) | 6.614 (4,111,500) | 6.555 (3,589,200) |
| H39 | 6.092 (1,235,900) | 6.390 (2,454,700) | 6.241 *[2] (1,741,800) |
| | Experiment 2 | | |
| Water control | 6.446 (2,792,500) | 6.521 (3,318,900) | 6.484 (3,047,900) |
| H39 | 6.222 (1,667,200) | 6.413 (2,588,200) | 6.317 * (2,074,900) |

*Fusarium culmorum* was applied at a concentration of $1 \times 10^2$ spores ml$^{-1}$ and $1 \times 10^3$ spores ml$^{-1}$ 18 hrs before H39 was applied with $2 \times 10^6$ spores ml$^{-1}$.
[1] Mean of 5 replicates, each with 4 straw segments; backtransformed values in brackets.
[2] Significantly different from control treatment (LSD-test; = 0.05).

TABLE 19

Effect of *Cladosporium cladosporioides* H39 on sporulation of *Alternaria brassicicola* on necrotic white cabbage leaves incubated in moist chamber at 24° C. for 9 days.

| | Sporulation index of *Alternaria brassicicola* [1] | | |
|---|---|---|---|
| Treatment | $1 \times 10^2$ spores ml$^{-1}$ | $1 \times 10^3$ spores ml$^{-1}$ | Mean |
| | Experiment 1 | | |
| Water control | 72.5 | 80.0 | 76.2 |
| H39 | 2.5 | 23.2 | 12.9 *[2] |
| | Experiment 2 | | |
| Water control | 78.8 | 87.5 | |
| H39 | 11.5 * | 41.8 * | |

*Alternaria brassicicola* was applied at a concentration of $1 \times 10^2$ spores ml$^{-1}$ and $1 \times 10^3$ spores ml$^{-1}$ 18 hrs before H39 was applied with $2 \times 10^6$ spores ml$^{-1}$.
[1] Mean of 5 replicates, each with 4 leaf segments.
[2] Significantly different from control treatment (LSD-test; = 0.05).

TABLE 20

Effect of *Cladosporium cladosporioides* H39 on fruit rot caused by *Monilla fructigena* on apples cv Elstar incubated in moist chamber at 24° C. for 8 and 12 days.

a. Number of lesions produced per 8 wounds.

| | Number of lesions [1] | | |
|---|---|---|---|
| Treatment | $1 \times 10^2$ spores ml$^{-1}$ | $1 \times 10^3$ spores ml$^{-1}$ | Mean |
| | Day 8 | | |
| Water control | 4.8 | 8.0 | 6.4 |
| H39 | 1.8 | 6.6 | 4.2 *[2] |
| | Day 12 | | |
| Water control | 8.0 | 6.4 | 7.2 |
| H39 | 7.4 | 5.4 | 6.4 |

TABLE 20-continued

Effect of *Cladosporium cladosporioides* H39 on fruit rot caused by *Monilla fructigena* on apples cv Elstar incubated in moist chamber at 24° C. for 8 and 12 days.

b. Average lesion diameter.

| | Lesion diameter (mm) [1] | | |
|---|---|---|---|
| Treatment | $1 \times 10^2$ spores ml$^{-1}$ | $1 \times 10^3$ spores ml$^{-1}$ | Mean |
| | Day 8 | | |
| Water control | 19.0 | 43.1 | 31.1 |
| H39 | 5.6 | 24.7 | 15.2 *[2] |
| | Day 12 | | |
| Water control | 53.3 | 85.7 | 69.5 |
| H39 | 31.1 | 66.2 | 48.6 * |

*Cladosporium cladosporioides* H39 was applied to wounds using 50 l spore suspension at $2 \times 10^6$ spores ml$^{-1}$. After 24 hrs, *Monilla fructigena* were applied using 50 l suspension at $1 \times 10^2$ spores and mycelial fragments ml$^{-1}$ and $1 \times 10^3$ spores and mycelial fragments ml$^{-1}$.
[1] Mean of 5 replicates, each with 4 apples with 2 treated wounds per apple.
[2] Significantly different from control treatment (LSD-test; = 0.05).

The invention claimed is:
1. A method of controlling a plant pathogen infection comprising:
spraying a composition comprising a *Cladosporium* to control the plant pathogen infection, the *Cladosporium* consisting of *Cladosporium cladosporioides* H39, as deposited on 13 Dec. 2007 under number CBS 122244 with the Centraal Bureau Schimmelcultures, Baarn, The Netherlands.

2. The method of claim 1, wherein the plant pathogen is selected from the group consisting of a plant pathogen of leaves, a plant pathogen of fruits, a plant pathogen of ears, and combinations of any thereof.

3. The method of claim 1, wherein the plant pathogen is selected from the group consisting of apple scab (*Venturia inaequalis*), pear scab (*Venturia pirina*), leaf spot (*Blumeriella jaapi*), rose black spot (*Diplocarpon rosae/Marssonina rosae*), brown spot (*Stemphylium vesicarium*), powdery mildew (*Podosphaera leucotricha/Sphaerotheca pannosa*), *begonia* mildew (*Microsphaera begoniae*), strawberry powdery mildew (*Sphaerotheca macularis*), sooty blotch (*Gloeodes pomigena*), fly speck (*Zygophalia jamaicensis*), peach leaf curl (*Taphrina deformans*), brown rot/spur canker (*Monilia fructigena, M. laxa*), pear rust (*Gymnosporangium sabinae/G. fuscum*), canker (*Nectria galligena*), rose black spot (*Diplocarpon rosae*), rust on roses (*Phragmidium tuberculatum/Phragmidium* spp.), *Botrytis* spp. in various plants, *Mycosphaerella brassicicola* in cabbage, *Mycosphaerella fifiensis* in banana, *Alternaria* spp. in *Brassica*, potato and various other plants, *Fusarium* spp. especially in cereals including maize, *Phytophthora infestans* of potato, *Plasmopara viticola* in grapevine, and combinations of any thereof.

4. The method of claim 3, wherein said plant pathogen comprises apple scab (*Venturia inaequalis*).

5. The method of claim 1, wherein the *Cladosporium* is present as spores.

6. The method of claim 5, the composition further comprising a carrier for the *Cladosporium* spores.

7. The method of claim 6, wherein the carrier comprises glucose.

8. The method of claim 1, wherein the *Cladosporium* comprises an extract of the *Cladosporium*.

9. The method of claim 1, wherein using the composition comprises spraying the composition on a part of a plant selected from the group consisting of the leaves, the fruits, the ears, and combinations of any thereof.

10. The method of claim 1, wherein controlling the pathogen comprises preventing infection by the pathogen.

11. The method of claim 1, wherein controlling the pathogen comprises decreasing plant damage caused by the pathogen.

12. The method of claim 1, wherein using the composition further comprises applying the composition pre-harvest.

13. The method of claim 1, wherein using the composition further comprises applying the composition post-harvest.

* * * * *